US008790905B2

(12) United States Patent
Aisaka et al.

(10) Patent No.: US 8,790,905 B2
(45) Date of Patent: Jul. 29, 2014

(54) FRUCTOSYL PEPTIDE OXIDASE

(71) Applicants: Kyowa Medex Co., Ltd, Tokyo (JP); Toshiko Aisaka, Machida (JP)

(72) Inventors: Kazuo Aisaka, Machida (JP); Keiko Suzuki, Machida (JP)

(73) Assignee: Kyowa Medex Co., Ltd., Chuo-ku, Tokyo (JP)

(*) Notice: Subject to any disclaimer, the term of this patent is extended or adjusted under 35 U.S.C. 154(b) by 64 days.

(21) Appl. No.: 13/633,410

(22) Filed: Oct. 2, 2012

(65) Prior Publication Data
US 2014/0057333 A1 Feb. 27, 2014

Related U.S. Application Data

(62) Division of application No. 13/123,049, filed as application No. PCT/JP2009/067565 on Oct. 8, 2009, now Pat. No. 8,304,249.

(30) Foreign Application Priority Data

Oct. 9, 2008 (JP) ................. 2008-262601

(51) Int. Cl.
*C07K 1/00* (2006.01)
*C12N 15/00* (2006.01)
*C12N 1/20* (2006.01)
*C12N 9/04* (2006.01)

(52) U.S. Cl.
USPC ............... 435/190; 435/252.3; 435/320.1; 530/350

(58) Field of Classification Search
USPC .............. 435/190, 252.3, 320.1; 530/350
See application file for complete search history.

(56) References Cited

U.S. PATENT DOCUMENTS

| 7,018,823 | B2 | 3/2006 | Kurosawa et al. |
| 7,070,948 | B1 | 7/2006 | Sakaue et al. |
| 7,329,520 | B2 | 2/2008 | Ebinuma |
| 7,393,549 | B2 | 7/2008 | Ebinuma |
| 7,588,910 | B2 | 9/2009 | Matsuoka et al. |
| 2009/0239239 | A1 | 9/2009 | Hirokawa et al. |

FOREIGN PATENT DOCUMENTS

| JP | 2001-095598 | | 4/2001 |
| JP | 2003-235585 | | 8/2003 |
| JP | 2010-035469 | A | 2/2010 |
| WO | WO 2004/038033 | A1 | 5/2004 |
| WO | WO 2004/038034 | A1 | 5/2004 |
| WO | WO 2004/104203 | A1 | 12/2004 |
| WO | WO 2007/125779 | A1 | 11/2007 |
| WO | WO 2011/015326 | A2 | 2/2011 |

OTHER PUBLICATIONS

Database Geneseq (online). "*Emericella nidulans* amadoriase," A0B50785; May 15, 2008.
Davis et al., "A High-Performance Liquid Chromatography Method for Hemoglobin $A_{1c}$," *Diabetes* 27(2)102-107 (1978).
Finke et al., "Preparation of a Candidate Primary Reference Material for the International Standardisation of HbA1c Determinations," *Clin. Chem. Lab. Med.* 36(5):299-308 (1998).
Fujiwara et al,. "Alternation of substrate specifically of fructosyl-amino acid oxidase from *Ulocladium* sp. JS-103," *J. Biosci. Bioeng.* 102(3): 241-243 (2006).
Hirowaka et al., "Enhancement of Thermostability of Fungal Deglycating Enzymes by Directed Evolution," *Appl. Microbiol. Biotechnol.* 78(5):775-781 (2008).
Hirokawa el al., "Molecular Cloning and Expression of Novel Fructosyl Peptide Oxidases and Their Application for the Measurement of Glycated Protein," *Biochem. Biophys. Res. Commun.* 311(1):104-111 (2003).
Jeong et al., "The VeA gene is necessary for the inducible expression by fructosyl amines of the *Aspergillus nindulans* faoA gene encoding fructosyl amino acid oxidase (amadoriase, EC 1.5.3)," *Arch. Microbiol.* 178: 344-350 (2002).
Katayama et al., "Tina-Quant HbA1c, A Homogenous Immunoturbidimetric Method for Hemoglobin A1c," *The Journal for the Japan Society for Clinical Laboratory Automation* 18(4):620 (1993). (English Language Translation provided).
NCBI GenPept Accession No. AF416568.1, Oct. 15, 2002.
Yoshida et al,. "Primary structures of fungal fructosyl amino acid oxidases and their application to the measurement of glycated proteins," *Eur. J. Biochem.* 242(3): 499-505 (1996).
English language translation of the International Preliminary Report on Patentability for International Application No. PCT/JP2009/067565 mailed Jun. 16, 2011.
International Search Report for International Application No. PCT/JP2009/067565, dated Nov. 9, 2009 (dated of completion of search) and Nov. 17, 2009 (date of mailing of report).
Office Action for U.S. Appl. No. 13/123,049, dated Jan. 3, 2012.
Supplementary European Search Report from European Patent Application No. 09819249.5 completed Mar. 14, 2012, mailed Mar. 27, 2012. (5 pages).

*Primary Examiner* — Maryam Monshipouri
(74) *Attorney, Agent, or Firm* — Clark & Elbing LLP

(57) ABSTRACT

The present invention encompasses:
[1] a DNA encoding the protein of any one of (i) a protein comprising the sequence of SEQ ID NO:1; (ii) a protein comprising a sequence with one to ten amino acid deletions, substitutions, or additions in the sequence of SEQ ID NO:1, and having fructosyl peptide oxidase activity;
(iii) a protein comprising a sequence having 99% or higher homology to the sequence of SEQ ID NO:1, and having fructosyl peptide oxidase activity; and (iv) a protein having fructosyl peptide oxidase activity, which is encoded by an expression plasmid harbored by the strain deposited under Accession No. FERM BP-11026;
[2] a DNA comprising the of SEQ ID NO: 2; and
[3] a DNA that hybridizes under stringent conditions with a DNA comprising a sequence complementary to SEQ ID NO: 2, where the DNA encodes a protein having fructosyl peptide oxidase activity.

16 Claims, 5 Drawing Sheets

SEQ ID NO: 1  (amino acid sequence of FPOX-9, 438 aa)
>FPOX-9
MAPRANTKIIVVGGGGTMGSSTALHLLRAGYTPSNITVLDTYPIPSAQSA
GYDLNKIMSIRLRNKPDLQLYLEALDMWKNDPLFKPFFHNVGQMDVSSTE
EGIKGLRMRYQSLLDAGIGLEKTNFLLESEDEILAKAPHFTREQIKGWKG
LFCGDGGWLAAAKAINAIGQFLKEQGVKFGFGGAGTFKKPLFADADEKTC
IGVETVDGTKYYADKVVLAAGAWSSTLVDLEEQCVSKAWVFAHIQLTPAE
AAAYKNTPVIYDGDYGFFIEPNENGIIKVCDEFPGFTHFKMHQPYGSPVP
KPISVPRSHAKHPTDTYPHASEVTIKKAINRFLPRFNDKELFNRAMCWCT
DTADANLLVCEHPRWKGFYLATGDSGHSFKLLPNIGKHVVELLEGRLESV
FKDAWRWRPGSGDALKSRRAAPAKDLADMPGWRNEAKM

FIG. 2

```
SEQ ID NO: 2    (DNA sequence of FPOX-9, 1,317-nt)
>FPOX-9
ATGGCGCCCCGAGCCAACACCAAAATCATCGTCGTCGGCGGCGGCGGCACAATGGGCTCG
TCGACAGCCCTACACCTCCTGCGCGCCGGCTACACGCCGTCCAACATCACAGTGCTCGAC
ACGTACCCTATCCCTTCCGCACAGTCTGCAGGCTACGACCTGAACAAAATCATGAGCATC
AGGCTGCGCAACAAGCCTGACTTACAACTCTATCTTGAGGCGCTGGACATGTGGAAAAAT
GATCCTCTATTCAAGCCGTTTTTCCACAATGTTGGACAGATGGACGTCTCTTCAACAGAA
GAAGGCATCAAAGGTCTTCGCATGAGATACCAGTCTCTTCTCGACGCAGGCATTGGGCTC
GAGAAGACGAATTTCCTGCTGGAAAGTGAAGACGAGATCCTGGCTAAAGCGCCGCATTTC
ACGCGGGAGCAGATTAAAGGCTGGAAAGGGCTGTTCTGTGGCGACGGCGGTTGGCTCGCT
GCAGCCAAAGCCATCAATGCCATCGGGCAGTTCCTCAAGGAACAGGGCGTCAAGTTTGGA
TTTGGCGGGGCCGGCACGTTCAAAAAGCCACTCTTCGCCGATGCCGACGAGAAGACGTGC
ATCGGCGTCGAAACTGTAGACGGCACAAAATACTACGCCGACAAGGTCGTTCTAGCAGCT
GGTGCCTGGAGTTCGACGTTGGTCGATCTGGAGGAGCAGTGCGTTTCAAAGGCCTGGGTC
TTTGCCCACATCCAACTGACGCCCGCTGAAGCAGCCGCGTACAAGAACACTCCTGTTATA
TACGACGGTGACTATGGGTTTTTCATTGAGCCGAATGAGAACGGCATCATAAAAGTCTGC
GACGAATTCCCTGGCTTCACGCACTTCAAGATGCACCAGCCGTACGGCTCACCGGTGCCC
AAACCCATCTCTGTGCCTCGCTCCCATGCGAAGCACCCCACAGATACATACCCGCACGCG
TCGGAGGTCACCATCAAAAAGGCTATCAACCGGTTCCTGCCGAGGTTCAATGACAAGGAA
CTGTTTAACAGGGCCATGTGCTGGTGCACCGATACCGCGGATGCAAATCTGCTTGTTTGT
GAGCATCCACGCTGGAAGGGGTTTTATCTTGCAACAGGGGACAGCGGGCATTCGTTCAAG
TTGCTGCCGAATATTGGAAAGCACGTTGTCGAGTTATTGGAGGGGAGGCTGGAAAGTGTG
TTTAAGGATGCTTGGAGGTGGAGGCCTGGCAGTGGGGATGCATTAAAGAGTAGACGGGCT
GCGCCTGCGAAGGACCTGGCGGATATGCCGGGGTGGAGGAATGAGGCAAAGATGTAG
```

FIG. 3

```
SEQ ID NO: 3    (amino acid sequence of FPOX-15, 438 aa)
>FPOX-15
MAPRANTKIIVVGGGGTMGSSTALHLLRAGYTPSNITVLDTYPIPSAQSA
GYDLNKIFGIRLRNKPDLQLYLEALDMWKNDPLFKPFFHNVGQMDVSSTE
EGIKKLRMRYQSLLDAGIGLEKTNFLLESEDEILAKAPHFTREQIKGWKG
LFCGDGGWLAAAKAINAIGQFLKEQGVKFGFGEAGTFKKPLFADADEKTC
IGVETVDGTKYYADKVVLAAGAWSSTLVDLEEQCVSKAWVFAHIQLTPAE
AAAYKNTPVIYDGDYGFFIEPDENGIIKVCDEFPGFTHFKMHQPYGSPVP
KLISVPRSHAKHPTDTYPHASEVTIKKAINRFLPRFNDKELFNRAMCWCT
DTADANLLVCEHPRWKGFYLATGDSGHSFKLLPNIGKHVVELLEGRLESV
FKDAWRWRPGSGDALKSRRAAPAKDLADMPGWRNEAKM
```

FIG. 4

```
SEQ ID NO: 4    (DNA sequence of FPOX-15, 1317-nt)
>FPOX-15
ATGGCGCCCCGAGCCAACACCAAAATCATCGTCGTCGGCGGCGGCGGCACAATGGGCTCG
TCGACAGCCCTACACCTCCTGCGCGCCGGCTACACGCCGTCCAACATCACAGTGCTCGAC
ACGTACCCTATCCCTTCCGCACAGTCTGCAGGCTACGACCTGAACAAAATCTTCGGCATC
AGGCTGCGCAACAAGCCTGACTTACAACTCTATCTTGAGGCGCTGGACATGTGGAAAAAT
GATCCTCTATTCAAGCCGTTTTTCCACAATGTTGGACAGATGGACGTCTCTTCAACAGAA
GAAGGCATCAAAAAGCTTCGCATGAGATACCAGTCTCTTCTCGACGCAGGCATTGGGCTC
GAGAAGACGAATTTCCTGCTGGAAAGTGAAGACGAGATCCTGGCTAAAGCGCCGCATTTC
ACGCGGGAGCAGATTAAAGGCTGGAAAGGGCTGTTCTGTGGCGACGGCGGTTGGCTCGCT
GCAGCCAAAGCCATCAATGCCATCGGGCAGTTCCTCAAGGAACAGGGCGTCAAGTTTGGA
TTTGGCGAGGCCGGCACGTTCAAAAAGCCACTCTTCGCCGATGCCGACGAGAAGACGTGC
ATCGGCCTCGAAACTGTAGACGGCACAAAATACTACGCCGACAAGGTCCTTCTAGCACCT
GGTGCCTGGAGTTCGACGTTGGTCGATCTGGAGGAGCAGTGCGTTTCAAAGGCCTGGGTC
TTTGCCCACATCCAACTGACGCCCGCTGAAGCAGCCGCGTACAAGAACACTCCTGTTATA
TACGACGGTGACTATGGGTTTTTCATTGAGCCGGACGAGAACGGCATCATAAAAGTCTGC
GACGAATTCCCTGGCTTCACGCACTTCAAGATGCACCAGCCGTACGGCTCACCGGTGCCC
AAATTGATCTCTGTGCCTCGCTCCCATGCGAAGCACCCCACAGATACATACCCGCACGCG
TCGGAGGTCACCATCAAAAAGGCTATCAACCGGTTCCTGCCGAGGTTCAATGACAAGGAA
CTGTTTAACAGGGCCATGTGCTGGTGCACCGATACCGCGGATGCAAATCTGCTTGTTTGT
GAGCATCCACGCTGGAAGGGGTTTTATCTTGCAACAGGGGACAGCGGGCATTCGTTCAAG
TTGCTGCCGAATATTGGAAAGCACGTTGTCGAGTTATTGGAGGGGAGGCTGGAAAGTGTG
TTTAAGGATGCTTGGAGGTGGAGGCCTGGCAGTGGGGATGCATTAAAGAGTAGACGGGCT
GCGCCTGCGAAGGACCTGGCGGATATGCCGGGGTGGAGGAATGAGGCAAAGATGTAG
```

FIG. 5

FRUCTOSYL PEPTIDE OXIDASE

CROSS-REFERENCE TO RELATED APPLICATIONS

This application is a divisional of U.S. patent application Ser. No. 13/123,049 now U.S. Pat. No. 8,304,249, which has a 371 (c) date of Jun. 2, 2011, which is the U.S. National Stage of International Application No. PCT/JP2009/067565, filed Oct. 8, 2009, which, in turn, claims benefit of Japanese Patent Application 2008-262601, filed Oct. 9, 2008.

TECHNICAL FIELD

The present invention relates to novel proteins having fructosyl peptide oxidase activity, DNAs encoding the proteins, methods for producing the proteins, methods for measuring glycated proteins using the proteins, and reagents for measuring glycated proteins comprising the proteins.

BACKGROUND ART

Glycated proteins are contained in biological samples such as body fluid and hair, and body fluid includes blood, and such. The concentration of glycated proteins present in the blood depends on the concentration of sugars such as glucose dissolved in the serum, and recently, in the field of clinical diagnosis, measurement of the concentration of hemoglobin A1c (Non-Patent Document 1), which is a glycated protein in the blood, is being used to diagnose and monitor diabetes mellitus. As methods for measuring this hemoglobin A1c, instrumental analytical methods using high performance liquid chromatography (HPLC) (Non-Patent Document 2), immunoassays using antigen-antibody reactions (for example, Non-Patent Document 3), and such had been known, but in recent years, enzymatic assays have been developed, and for example, a method using a protease and a fructosyl peptide oxidase (Patent Document 1) has been developed. Enzymatic assays can be applied to versatile automated analyzers, and since the operations are also simple, their development is increasing.

The fructosyl peptide oxidase used in enzymatic assays is an enzyme that catalyzes the reaction which produces a sugar osone (an α-keto aldehyde), a peptide, and hydrogen peroxide by oxidative cleaving, in the presence of oxygen molecules, the C—N bond in the ketose derivative produced by Amadori rearrangement of glucosylamine produced by the reaction between the hemiacetal of glucose and the N-terminal amino group of a peptide.

In the case of enzymatic assays, as shown in FIG. 1, a method is known in which hemoglobin A1c is first degraded with a protease, and α-fructosyl valyl histidine (hereinafter, denoted as α-FVH) is produced from the N terminus of the β-chain of hemoglobin; next, fructosyl peptide oxidase is made to act on the produced α-FVH, hydrogen peroxide which is produced is applied to oxidative condensation in the presence of peroxidase to afford a quinone dye, and the produced amount is determined by colorimetry using a spectrophotometer (Patent Document 1).

However, ε-fructosyl lysine and glycated peptides containing it form as byproducts by protease treatment, and it has been pointed out that there is a risk that, when fructosyl peptide oxidase acts on them, the measured values of hemoglobin A1c may be higher than the true values (Patent Document 2).

Fructosyl peptide oxidase has been found from bacteria, fungi, and plants. For example, fructosyl peptide oxidase derived from the genus *Achaetomiella*, the genus *Chaetomium* (Patent Document 3), the genus *Curvularia* (Patent Document 2), the Rosaceae family, the Vitaceae family, the Apiaceae family (Patent Document 4), the Zingiberaceae family (Patent Document 5), and such are known.

However, fructosyl peptide oxidases reported so far had drawbacks, such as:

(1) the activity towards an α-glycated dipeptide (α-fructosyl valyl histidine) in comparison to an α-glycated amino acid (for example, α-fructosyl valine) is not necessarily high;

(2) as described above, in addition to the N-terminal α-glycated dipeptide, it also acts on an ε-glycated amino acid in which a sugar is bound to the ε-amino group of lysine (ε-fructosyl lysine), and increases the measured values in hemoglobin A1c measurements; and (3) in the case of measurement methods using enzymes, the enzymes become unstable during measurement or storage.

To overcome these drawbacks, enzymes with decreased reactivity towards ε-fructosyl lysine as a result of artificial introduction of mutations into fructosyl peptide oxidase (Patent Document 4), enzymes with increased heat resistance also due to introduction of mutations (Non-Patent Document 4), and such have been reported. However, the existence of enzymes that have simultaneously overcome the above-mentioned drawbacks of (1) to (3) at a high level is still not known.

[Non-Patent Document 1] Clinical Chemistry and Laboratory Medicine Vol. 36, p. 299-308 (1998).

[Non-Patent Document 2] Chromatogr. Sci., Vol. 10, p. 659 (1979).

[Non-Patent Document 3] Nihon Rinsho Kensa Jidoka Gakkai Kaishi (Journal of the Japan Society for Clinical Laboratory Automation), Vol. 18, No. 4, p. 620 (1993).

[Non-Patent Document 4] Appl. Microbiol. Biotechnol., Vol. 78, No. 5, p. 775-781 (2008).

[Patent Document 1] Japanese Patent Application Kokai Publication No. (JP-A) 2001-95598 (unexamined, published Japanese patent application).

[Patent Document 2] International Publication No. WO 2004/104203 pamphlet.

[Patent Document 3] JP-A (Kokai) 2003-235585.

[Patent Document 4] International Publication No. WO 2004/038033 pamphlet.

[Patent Document 5] International Publication No. WO 2004/038034 pamphlet.

DISCLOSURE OF THE INVENTION

Problems to be Solved by the Invention

The present invention was achieved in view of the above-mentioned problems. An objective of the present invention is to provide proteins with high specificity towards an α-glycated dipeptide (α-fructosyl valyl histidine) and having very stable fructosyl peptide oxidase activity. Furthermore, another objective of the present invention is to provide DNAs encoding the proteins, recombinant DNAs containing the DNAs, transformant transformed with the recombinant DNAs, method for producing proteins having fructosyl peptide oxidase activity using the transformant and such, as well as method for measuring a glycated protein using the proteins, and reagent for measuring glycated proteins comprising the proteins.

Means for Solving the Problems

The present invention relates to the following (1) to (17):
(1) a protein of any one of [1] to [4] below:

[1] a protein comprising the amino acid sequence represented by SEQ ID NO: 1;
[2] a protein comprising an amino acid sequence with one or more amino acid deletions, substitutions, or additions in the amino acid sequence represented by SEQ ID NO: 1, and having fructosyl peptide oxidase activity;
[3] a protein comprising an amino acid sequence having 80% or higher homology to the amino acid sequence represented by SEQ ID NO: 1, and having fructosyl peptide oxidase activity; and
[4] a protein having fructosyl peptide oxidase activity, which is encoded by an expression plasmid harbored by the *Escherichia coli* XL1-Blue MRF' strain deposited under Accession No. FERM BP-11026;
(2) the protein of (1), comprising the amino acid sequence represented by SEQ ID NO: 3;
(3) a DNA of any one of [1] to [3] below:
[1] a DNA encoding the protein of (1);
[2] a DNA comprising the nucleotide sequence represented by SEQ ID NO: 2; and
[3] a DNA that hybridizes under stringent conditions with a DNA comprising a nucleotide sequence complementary to the nucleotide sequence represented by SEQ ID NO: 2, wherein the DNA encodes a protein having fructosyl peptide oxidase activity;
(4) the DNA of (3), encoding a protein comprising the amino acid sequence represented by SEQ ID NO: 3;
(5) the DNA of (3), comprising the nucleotide sequence represented by SEQ ID NO: 4; (6) a recombinant DNA comprising the DNA of any one of (3) to (5);
(7) a transformant comprising the recombinant DNA of (6);
(8) a method for producing the protein of (1) or (2), wherein the transformant of (7) is cultured in a medium, the protein is produced and accumulated in the culture, and the protein is collected from the culture;
(9) a method for measuring a glycated protein in a sample, wherein the method comprises reacting a sample with a protease to form a glycated peptide, then reacting the formed glycated peptide with the protein of (1) or (2), and measuring a substance formed by the reaction between the glycated peptide and the protein or a substance consumed in the reaction between the glycated peptide and the protein;
(10) the measurement method of (9), wherein the glycated protein is glycated hemoglobin;
(11) the measurement method of (10), wherein the glycated hemoglobin is hemoglobin A1c;
(12) a reagent for measuring a glycated protein, comprising a protease and the protein of (1) or (2);
(13) the reagent of (12), further comprising a reagent for measuring a product formed by a reaction between the protein of (1) or (2) and a glycated peptide formed from a glycated protein;
(14) the reagent of (13), wherein the product is hydrogen peroxide.
(15) the reagent of any one of (12) to (14), wherein the glycated protein is glycated hemoglobin;
(16) the reagent of (15), wherein the glycated hemoglobin is hemoglobin A1c; and
(17) *Escherichia coli* XL1-Blue MRF' strain deposited under Accession No. FERM BP-11026.

Effects of the Invention

The present invention provides proteins with high specificity towards an α-glycated dipeptide (α-fructosyl valyl histidine) and having very stable fructosyl peptide oxidase activity, DNAs encoding the proteins, methods for producing the proteins, as well as methods for measuring glycated proteins using the proteins, and reagents for measuring glycated proteins, which comprise the proteins.

BRIEF DESCRIPTION OF THE DRAWINGS

FIG. 2 shows the amino acid sequence of FPOX-9. Amino acids marked with a circle on top show mutated sites with respect to the amino acid sequence of the fructosyl peptide oxidase-producing fungus (genetic source).
FIG. 3 shows the DNA sequence of FPOX-9. Nucleotides marked with a circle on top show mutated sites with respect to the DNA sequence of the fructosyl peptide oxidase-producing bacterium (genetic source).
FIG. 4 shows the amino acid sequence of FPOX-15. Amino acids marked with a circle on top show sites mutated from those of the fructosyl peptide oxidase-producing bacterium (genetic source), and the underlined amino acids show mutated sites with respect to the amino acid sequence of FPOX-9.
FIG. 5 shows the DNA sequence of FPOX-15. Nucleotides marked with a circle on top show mutated sites with respect to the DNA sequence of the fructosyl peptide oxidase-producing bacterium (genetic source), and the underlined nucleotides show mutated sites with respect to the DNA sequence of FPOX-9.

MODE FOR CARRYING OUT THE INVENTION

Figure 1:
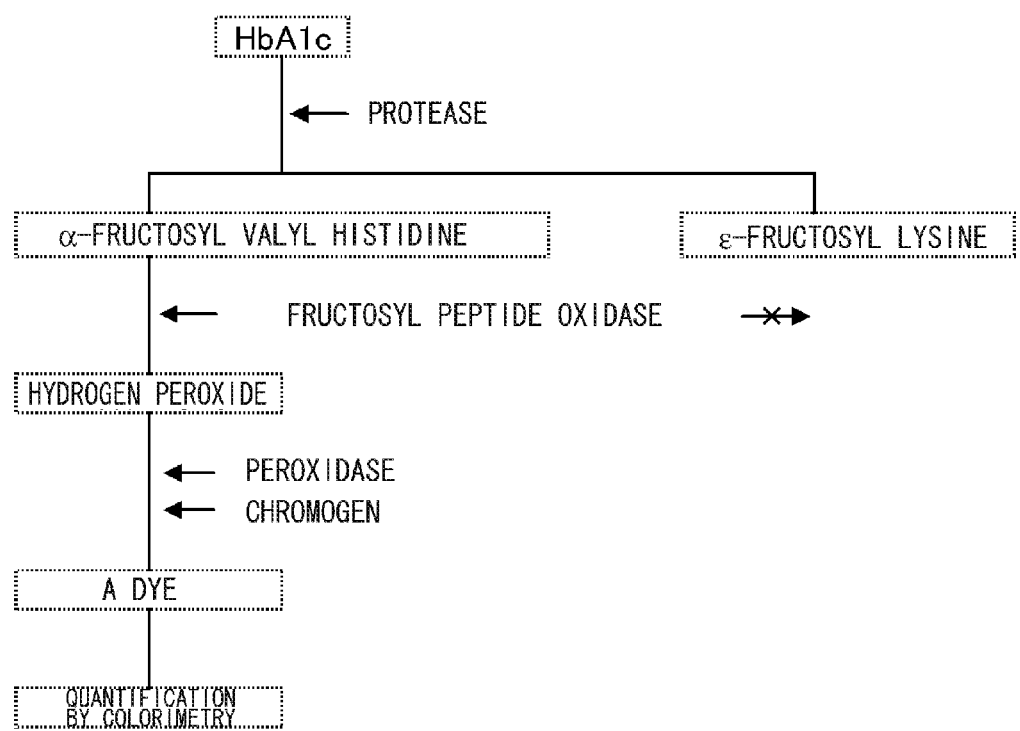
FIG. 1 shows a scheme of an enzymatic measurement of hemoglobin A1c.

1. The Proteins of the Present Invention

Examples of the proteins of the present invention include
[1] a protein comprising the amino acid sequence represented by SEQ ID NO: 1;
[2] a protein comprising an amino acid sequence with one or more amino acid deletions, substitutions, or additions in the amino acid sequence represented by SEQ ID NO: 1, and having fructosyl peptide oxidase activity;
[3] a protein comprising an amino acid sequence having 80% or higher homology to the amino acid sequence represented by SEQ ID NO: 1, and having fructosyl peptide oxidase activity; and
[4] a protein having fructosyl peptide oxidase activity, which is encoded by an expression plasmid carried by the *Escherichia coli* XL1-Blue MRF' strain deposited under Accession No. FERM BP-11026.

In the above, the protein comprising an amino acid sequence with one or more amino acid deletions, substitutions, or additions, and having fructosyl peptide oxidase activity can be obtained, for example, by introducing site-specific mutations to a DNA encoding a protein comprising the amino acid sequence represented by SEQ ID NO: 1 using site-specific mutagenesis methods described in Molecular Cloning, A Laboratory Manual, Second Edition, Cold Spring Harbor Laboratory Press (1989) (hereinafter, abbreviated as Molecular Cloning, Second Edition); Current Protocols in Molecular Biology, John Wiley & Sons (1987-1997) (hereinafter, abbreviated as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); and Proc. Natl. Acad. Sci. USA, 82, 488 (1985); and such.

While the number of amino acids that are deleted, substituted, or added is not particularly limited, it is a number that can be deleted, substituted, or added by known methods such as the above-mentioned site-specific mutagenesis methods, and the number is one to dozens, preferably one to 20, more preferably one to ten, and even more preferably one to five.

When one or more amino acids are deleted, substituted, or added to the amino acid sequence represented by SEQ ID NO: 1, one or more amino acids may be deleted, substituted, or added at any position in the same sequence.

The amino acid positions where amino acid deletions or additions can take place include, for example, one to several amino acids at the N-terminal side and the C-terminal side of the amino acid sequence represented by SEQ ID NO: 1.

Deletions, substitutions, or additions may occur simultaneously, and the substituted or added amino acids may be naturally-occurring type or non-naturally-occurring type amino acids. Examples of naturally-occurring type amino acids include L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, and L-cysteine.

Hereinafter, examples of mutually substitutable amino acids are shown. Amino acids included in the same group are mutually substitutable.

Group A: leucine, isoleucine, norleucine, valine, norvaline, alanine, 2-aminobutanoic acid, methionine, O-methylserine, t-butyl glycine, t-butyl alanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine Furthermore, in order for the proteins of the present invention to have fructosyl peptide oxidase activity, desirably, the proteins have 80% or higher, preferably 90% or higher, more preferably 94% or higher, more preferably 98% or higher, particularly preferably 99% or higher homology to the amino acid sequence represented by SEQ ID NO: 1.

Homology of amino acid sequences and nucleotide sequences can be determined using the BLAST algorithm by Karlin and Altshul [Pro. Natl. Acad. Sci. USA, 90, 5873 (1993)] or FASTA [Methods Enzymol., 183, 63 (1990)]. Programs called BLASTN and BLASTX have been developed based on this BLAST algorithm [J. Mol. Biol., 215, 403 (1990)]. When nucleotide sequences are analyzed by BLASTN based on BLAST, parameters are set, for example, at score=100 and wordlength=12. When amino acid sequences are analyzed by BLASTX based on BLAST, parameters are set, for example, at score=50 and wordlength=3. When using the BLAST and Gapped BLAST programs, the default parameters of each program are used.

A protein comprising an amino acid sequence having 80% or higher, preferably 90% or higher, more preferably 94% or higher, even more preferably 98% or higher, or particularly preferably 99% or higher homology to the amino acid sequence represented by SEQ ID NO: 1, and having fructosyl peptide oxidase activity is also a protein of the present invention.

A protein of the present invention is, for example, a protein comprising the amino acid sequence represented by SEQ ID NO: 3.

As means for confirming that the proteins of the present invention have fructosyl peptide oxidase activity, for example, one may produce a transformant that expresses the proteins of the present invention by a DNA recombination method, produce the proteins of the present invention using the transformant, then using α-FVH as a substrate, measure the hydrogen peroxide formed by the reaction with the substrate.

The proteins of the present invention have the following properties:
(a) action: oxidation of glycated peptide using molecular oxygen to afford a sugar osone (an α-keto aldehyde), a peptide, and hydrogen peroxide.
(b) substrate specificity: high reactivity towards α-FVH and low reactivity towards e-fructosyl lysine (hereinafter, abbreviated as ε-FK).

Proteins of the present invention can be confirmed to have high activity towards α-FVH and low reactivity towards ε-FK, for example, by using α-FVH and ε-FK as substrates and measuring the ratio of the activity for α-FVH to that for ε-FK (α-FVH/ε-FK).

The optimal pH and the range of stable pH of the fructosyl peptide oxidase activity of the proteins of the present invention are not particularly limited, and the optimal pH is preferably around 6.0 to 7.0, and the stable pH for treatment at 40° C. for ten minutes is preferably pH6.0 to 9.0.

The range of the optimal temperature for action is not particularly limited, and is preferably around 30° C. to 50° C. Higher the thermostability of the protein is, more preferred the protein is, and for example, the protein with residual activity of 25% or more after treatment at 50° C. for 15 minutes is used favorably.

Measurement of fructosyl peptide oxidase activity is carried out by the following method and the amount of enzyme that produces 1 mmol of hydrogen peroxide in one minute from α-FVH is defined as one unit (U).

Preparation of Reagents for Measuring the Activity
Solution A: Coloring Solution Solution A-1: Solution of 4-aminoantipyrine in ion-exchanged water with a concentration of 2.4 mmol/L.

Solution A-2: Solution of N-ethyl-N-(3-methylphenyl)-N'-succinylethylenediamine (EMSE) in ion-exchanged water with a concentration of 32 mmol/L.

Solution B: Peroxidase Solution

Solution of peroxidase (110 U/mg, manufactured by TOYOBO) in 0.1 mol/L phosphate buffer (pH7.0) with a concentration of 2 mg/mL.

Solution C: Substrate Solution

Solution of α-FVH or ε-FK (manufactured by PEPTIDE INSTITUTE) in 0.1 mol/L phosphate buffer (pH7.0) with a concentration of 10 mmol/mL.

Measurement Procedure

50 μL of solution A-1, 50 μL of solution A-2, 2 μL of solution B, and 20 μL of solution C were mixed and filled up with water to 200 μL, this was then preincubated at 30° C. for five minutes, then 1 μL of the enzyme solution was added, the mixture was allowed to react for 30 minutes at 30° C., and the absorbance at 550 nm was measured on a plate reader (infinite F200, manufactured by Tecan). For the blank value, measurement is taken on a solution prepared by using ion-exchanged water instead of the substrate solution (C solution).

Subsequently, various amounts of hydrogen peroxide are added to the above measurement system, the absorbance at 550 nm is measured, a calibration curve that shows the relationship between the amount of hydrogen peroxide and absorbance is produced, and from this, the unit number of the enzyme (the enzyme titer) is determined The *Escherichia coli* XL1-Blue MRF' strain carrying a plasmid (an expression plasmid) that expresses a protein comprising the amino acid sequence represented by SEQ ID NO: 1 (*Escherichia coli* XL1-Blue MRF'/pTrcFPOX-9) was deposited with International Patent Organism Depositary (IPOD) of the National Institute of Advanced Industrial Science and Technology (AIST). The contents specifying the deposit are described below.
(a) Name and Address of Depositary Institution
   Name: International Patent Organism Depositary (IPOD) of the National Institute of Advanced Industrial Science and Technology (AIST)
   Address: Tsukuba Central 6, 1-1-1 Higashi, Tsukuba, Ibaraki, Japan (Postal Code: 305-8566)
(b) Date of receipt (Date of deposit): Sep. 19, 2008
(c) Receipt No. (Accession No.): FERM BP-11026
   The *Escherichia coli* XL1-Blue MRF' strain deposited under the above-mentioned Accession No. FERM BP-11026, the expression plasmids carried by this bacterial strain, and the proteins having fructosylpeptide oxidase activity which are encoded by the plasmids are also included in the present invention.

2. The DNAs of the Present Invention

Examples of the DNAs of the present invention include:
[1] a DNA encoding the protein of the present invention according to [1] to [3] under 1 above;
[2] a DNA comprising the nucleotide sequence represented by SEQ ID NO: 2; and
[3] a DNA which hybridizes under stringent conditions with a DNA comprising a nucleotide sequence that is complementary to the nucleotide sequence represented by SEQ ID NO: 2, and which encodes a protein having fructosyl peptide oxidase activity.

Herein, "to hybridize" means that a DNA of interest hybridizes with a DNA having a specific nucleotide sequence or with a part of this DNA. Therefore, the nucleotide sequence of the DNA having a specific nucleotide sequence or the part of this DNA may be a DNA with a length which is useful as a probe for Northern or Southern blot analyses, or which can be used as an oligonucleotide primer for PCR analyses. DNAs used as a probe include DNAs of at least 100 nucleotides or more, preferably 200 nucleotides or more, or more preferably 500 nucleotides or more; and, they can also be DNAs of at least 10 nucleotides or more, or preferably 15 nucleotides or more.

Methods for hybridization experiments of DNAs are well known. The conditions for hybridization can be determined and experiments can be carried out, for example, according to the descriptions in Molecular Cloning, Second Edition, Third Edition (2001); Methods for General and Molecular Bacteriology, ASM Press (1994); Immunology methods manual, Academic press (Molecular), and many other standard textbooks.

Examples of the above-mentioned stringent conditions include conditions in which a filter with DNA immobilized onto it and a probe DNA are incubated in a solution containing 50% formamide, 5×SSC (750 mmol/L sodium chloride and 75 mmol/L sodium citrate), 50 mmol/L sodium phosphate (pH 7.6), 5×Denhardt's solution, 10% dextran sulfate and 20 µg/L denatured salmon sperm DNA at 42° C. overnight, and after incubation, the filter is washed, for example, in 0.2×SSC solution at approximately 65° C.; and, conditions with lower stringency can also be used. The stringent conditions can be modified by adjusting the concentration of formamide (the conditions become less stringent as the concentration of formamide is lowered) or by changing the salt concentrations and temperature conditions. Examples of low stringency conditions include conditions in which incubation is carried out in a solution containing 6×SSCE (20×SSCE: 3 mol/L sodium chloride, 0.2 mol/L sodium dihydrogenphosphate and 0.02 mol/L EDTA, pH 7.4), 0.5% SDS, 30% formamide, and 100 µg/L denatured salmon sperm DNA at 37° C. overnight, and then washing using a 1×SSC, 0.1% SDS solution at 50° C. Examples of still less stringent conditions include conditions in which hybridization is carried out under the above-mentioned low stringency conditions using a solution with a high salt concentration (for example, 5×SSC) followed by washing.

The various conditions described above can also be set by adding or changing a blocking reagent used to suppress the background of the hybridization experiments. The hybridization conditions may be changed following addition of the above-mentioned blocking reagent to make the conditions compatible.

The above-mentioned DNAs capable of hybridizing under stringent condition include DNA comprising a nucleotide sequence having a homology of at least 80% or more, preferably 90% or more, more preferably 94% or more, even more preferably 98% or more, or particularly preferably 99% or more to the nucleotide sequence represented by SEQ ID NO: 2, when calculated for example using programs such as BLAST and FASTA described above based on the above-mentioned parameters.

It is possible to confirm that a DNA hybridizing under stringent conditions with the above-mentioned DNA is a DNA encoding a protein having fructosyl peptide oxidase activity by preparing a recombinant DNA expressing the DNA, introducing the recombinant DNA into host cells, culturing the obtained microorganisms, purifying the protein obtained from the culture, and by using the purified protein as an enzyme source and α-FVH as a substrate, measuring hydrogen peroxide produced by reaction with the substrate.

Examples of the DNAs of the present invention include DNAs encoding a protein comprising the amino acid sequence represented by SEQ ID NO: 3, and DNAs comprising the nucleotide sequence represented by SEQ ID NO: 4.

3. The Transformants of the Present Invention

Examples of the transformants of the present invention include transformants obtained by transforming host cells by a known method using a recombinant DNA containing a DNA of the above 2. Examples of host cells include bacteria, yeast, animal cells, insect cells and plant cells, and are preferably bacteria, more preferably prokaryotic cells, and even more preferably microorganisms belonging to the genus *Escherichia*.

4. Preparation of the DNAs of the Present Invention

The DNAs of the present invention can be obtained, for example, from a microorganism such as filamentous fungus, preferably from a microorganism belonging to the genus *Aspergillus* or the genus *Emericella*, or particularly preferably from a microorganism belonging to *Emericella nidulans* and such, using probes that can be designed based on the nucleotide sequence represented by SEQ ID NO: 2.

Alternatively, based on various genetic sequence databases, can be searched a sequence having a homology of 85% or more, preferably 90% or more, more preferably 95% or more, even more preferably 98% or more, and particularly preferably 99% or more to the nucleotide sequence of a DNA encoding the amino acid sequence represented by SEQ ID NO: 1, and based on the nucleotide sequence obtained by the search, the DNA of the present invention or DNA used in the production method of the present invention can also be obtained according to the above-described methods from a chromosomal DNA, cDNA library, or such of an organism having the nucleotide sequence.

The nucleotide sequence of the DNA can be determined by using the obtained DNA as is or by cleaving it with appropriate restriction enzymes, inserting it into a vector by a conventional method, introducing the obtained recombinant DNA into host cells, then analyzing using a conventionally used nucleotide sequence analysis method such as the dideoxy method [Proc. Natl. Acad. Sci., USA, 74, 5463 (1977)] or a nucleotide sequence analyzer such as the 373A DNA Sequencer (manufactured by Perkin Elmer).

Examples of vectors for inserting the DNA of the present invention include pBluescript II KS(+) (manufactured by Stratagene), pDIRECT [Nucleic Acids Res., 18, 6069 (1990)], pCR-Script Amp SK(+) (manufactured by Stratagene), pT7Blue (manufactured by Novagen, Inc.), pCR II (manufactured by Invitrogen Corp.) and pCR-TRAP (manufactured by GenHunter Corp.).

As host cell, microorganisms belonging to the genus *Escherichia* and such can be used. Examples of microorganisms belonging to the genus *Escherichia* include *Escherichia coli* XL1-Blue, *Escherichia coli* XL2-Blue, *Escherichia coli* DH1, *Escherichia coli* MC1000, *Escherichia coli* ATCC 12435, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Escherichia coli* BL21 and *Escherichia coli* ME8415.

As a method for introducing recombinant DNA, any of the methods for introducing DNA into the above host cells can be used, and examples include methods using calcium ion [Proc. Natl. Acad. Sci. USA, 69, 2110 (1972)], the protoplast method (JP-A (Kokai) S63-248394), and electroporation [Nucleic Acids Res., 16, 6127 (1988)].

In case that the obtained DNA was a partial DNA as a result of nucleotide sequence determination, the full length DNA can be obtained by Southern hybridization or such on a chromosomal DNA library using the partial DNA as a probe.

Further, it is also possible to prepare the desired DNA by chemical synthesis using a Model 8905 DNA synthesizer manufactured by PerSeptive Biosystems or the like, based on the determined nucleotide sequence of the DNA.

An example of the DNA obtained as described above is a DNA having the nucleotide sequence represented by SEQ ID NO: 2.

5. Methods for Producing Transformants Used in the Production Methods of the Present Invention Based on the DNA of the present invention, a DNA fragment of an appropriate length containing a region encoding a protein of the present invention is prepared as necessary. A transformant with improved protein production rate can be obtained by substituting nucleotides in the nucleotide sequence of the portion encoding the protein so as to obtain codons that are optimal for expression in a host.

A recombinant DNA is generated by inserting the DNA fragment downstream of a promoter in an appropriate expression vector.

A transformant which produces the protein of the present invention can be obtained by introducing the recombinant DNA into a host cell appropriate for the expression vector.

As host cell, any host cell such as bacterial cell, yeast cell, animal cell, insect cell, and plant cell can be used, so long as it is capable of expressing the gene of interest.

The expression vectors that are employed are those capable of autonomous replication or integration into the chromosome in the above-mentioned host cells, and containing a promoter at a position that enables transcription of the DNA of the present invention.

In case of using a prokaryote such as a bacterium as the host cell, the recombinant DNA containing the DNA of the present invention is preferably a recombinant DNA which is capable of autonomous replication in the prokaryote and, at the same time, is composed of a promoter, a ribosome binding sequence, a DNA of the present invention, and a transcription termination sequence. A gene regulating the promoter may also be included.

Examples of expression vectors are pCold I (manufactured by TAKARA BIO Inc.), pCDF-1b and pRSF-1b (both manufactured by Novagen Inc.), pMAL-c2x (manufactured by New England Biolabs Inc.), pGEX-4T-1 (manufactured by GE Healthcare Biosciences), pTrcHis (manufactured by Invitrogen Corp.), pSE280 (manufactured by Invitrogen Corp.), pGEMEX-1 (manufactured by Promega Corp.), pQE-30 (manufactured by Qiagen Inc.), pET-3 (manufactured by Novagen Inc.), pKYP10 (JP-A (Kokai) S58-110600), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(−) (manufactured by Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO 98/12343), pUC19 [Gene, 33, 103 (1985)], pSTV28 (manufactured by TAKARA BIO Inc.), pUC118 (manufactured by TAKARA BIO Inc.) and pPA1 (JP-A (Kokai) S63-233798).

Any promoter can be used so long as it can function in host cells such as *Escherichia coli*. Examples include promoters derived from *Escherichia coli*, phages, or the like, such as the trp promoter ($P_{trp}$), lac promoter ($P_{lac}$), $P_L$ promoter, $P_R$ promoter, and $P_{SE}$ promoter, as well as the SPO1 promoter, SPO2 promoter, and penP promoter. Promoters with artificial design changes can also be used, such as a promoter in which two $P_{trp}$ are arranged in tandem, the tac promoter, lacT7 promoter, and let I promoter.

Furthermore, the xylA promoter for expression in microorganisms belonging to the genus *Bacillus* [Appl. Microbiol. Biotechnol., 35, 594-599 (1991)], the P54-6 promoter for expression in microorganisms belonging to the genus *Corynebacterium* [Appl. Microbiol. Biotechnol., 53, 674-679 (2000)], and such can also be used.

Use of a plasmid in which the distance between the Shine-Dalgarno sequence, which is a ribosome binding sequence, and the initiation codon is appropriately adjusted (for example, 6 to 18 nucleotides) is preferred.

In a recombinant DNA in which the DNA of the present invention has been ligated to an expression vector, a transcription termination sequence is not always necessary; however, a transcription termination sequence is preferably placed immediately downstream of a structural gene.

An example of such recombinant DNA is pET21-plu1440.

Examples of prokaryotes include microorganisms belonging to the genera *Escherichia, Serratia, Bacillus, Brevibacterium, Corynebacterium, Microbacterium, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus* and *Zymomonas*. For example, they are *Escherichia coli* XL1-Blue, *Escherichia coli* XL2-Blue, *Escherichia coli* DH1, *Escherichia coli* DH5α, *Escherichia coli* MC1000,

*Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* MP347, *Escherichia coli* NM522, *Escherichia coli* BL21, *Bacillus subtilis* ATCC 33712, *Bacillus megaterium*, *Brevibacterium ammoniagenes*, *Brevibacterium immariophilum* ATCC 14068, *Brevibacterium saccharolyticum* ATCC 14066, *Brevibacterium flavum* ATCC 14067, *Brevibacterium lactofermentum* ATCC 13869, *Corynebacterium glutamicum* ATCC 13032, *Corynebacterium glutamicum* ATCC 14297, *Corynebacterium acetoacidophilum* ATCC 13870, *Microbacterium ammoniaphilum* ATCC 15354, *Serratia ficaria*, *Serratia fonticola*, *Serratia liquefaciens*, *Serratia marcescens*, *Pseudomonas* sp. D-0110, *Agrobacterium radiobacter*, *Agrobacterium rhizogenes*, *Agrobacterium rubi*, *Anabaena cylindrica*, *Anabaena doliolum*, *Anabaena flos-aquae*, *Arthrobacter aurescens*, *Arthrobacter citreus*, *Arthrobacter globiformis*, *Arthrobacter hydrocarboglutamicus*, *Arthrobacter mysorens*, *Arthrobacter nicotianae*, *Arthrobacter paraffineus*, *Arthrobacter protophormiae*, *Arthrobacter roseoparaffinus*, *Arthrobacter sulfureus*, *Arthrobacter ureafaciens*, *Chromatium buderi*, *Chromatium tepidum*, *Chromatium vinosum*, *Chromatium warmingii*, *Chromatium fluviatile*, *Erwinia uredovora*, *Erwinia carotovora*, *Erwinia ananas*, *Erwinia herbicola*, *Erwinia punctata*, *Erwinia terreus*, *Methylobacterium rhodesianum*, *Methylobacterium extorquens*, *Phormidium* sp. ATCC 29409, *Rhodobacter capsulatus*, *Rhodobacter sphaeroides*, *Rhodopseudomonas blastica*, *Rhodopseudomonas marina*, *Rhodopseudomonas palustris*, *Rhodospirillum rubrum*, *Rhodospirillum salexigens*, *Rhodospirillum salinarum*, *Streptomyces ambofaciens*, *Streptomyces aureofaciens*, *Streptomyces aureus*, *Streptomyces fungicidicus*, *Streptomyces griseochromogenes*, *Streptomyces griseus*, *Streptomyces lividans*, *Streptomyces olivogriseus*, *Streptomyces rameus*, *Streptomyces tanashiensis*, *Streptomyces vinaceus*, and *Zymomonas mobilis*.

As a method for introducing a recombinant DNA into a prokaryote, any method can be used so long as it introduces the DNA into the above-mentioned host cells, and examples include the method using calcium ion [Proc. Natl. Acad. Sci. USA, 69, 2110 (1972)], the protoplast method (JP-A (Kokai) S63-248394), and the electroporation method [Nucleic Acids Res., 16, 6127 (1988)].

In case of using an yeast strain as the host cell, YEp13 (ATCC 37115), YEp24 (ATCC 37051), YCp50 (ATCC 37419), pHS19, and pHS15 can be used as the expression vector.

As a promoter, any promoter can be used so long as it will function in an yeast strain, and examples include promoters such as the PHO5 promoter, the PGK promoter, the GAP promoter, the ADH promoter, the gal 1 promoter, the gal 10 promoter, the heat shock polypeptide promoter, the MFα1 promoter, and the CUP 1 promoter.

Examples of the host cells include yeast strains belonging to the genera *Saccharomyces*, *Schizosaccharomyces*, *Kluyveromyces*, *Trichosporon*, *Schwanniomyces*, *Pichia*, and *Candida*, and specific examples include *Saccharomyces cerevisiae*, *Schizosaccharomyces pombe*, *Kluyveromyces lactis*, *Trichosporon pullulans*, *Schwanniomyces alluvius*, *Pichia pastoris*, and *Candida utilis*.

As a method for introducing the recombinant DNA into yeast, any method can be used so long as it will introduce the DNA into yeast, and examples include the electroporation method [Methods Enzymol., 194, 182 (1990)], the spheroplast method [Proc. Natl. Acad. Sci. USA, 81, 4889 (1984)], and the lithium acetate method [J. Bacteriol., 153, 163 (1983)].

In case of using an animal cell as the host cell, pcDNAI, pcDM8 (commercially available from Funakoshi Co., Ltd.), pAGE107 (JP-A (Kokai) H03-22979), pAS3-3 (JP-A (Kokai) H02-227075), pCDM8 [Nature, 329, 840 (1987)], pcDNAI/Amp (manufactured by Invitrogen Corp.), pREP4 (manufactured by Invitrogen Corp.), pAGE103 [J. Biochem., 101, 1307 (1987)], pAGE210, pAMo, pAMoA, and such can be used as the expression vector.

As a promoter, any promoter can be used so long as it will function in animal cells, and examples include the promoter of the immediate early (1E) gene of cytomegalovirus (CMV), SV40 early promoter or metallothionein promoter, the promoter of a retrovirus, heat shock promoter, SRα promoter, and such. Further, the enhancer of the IE gene of human CMV can be used in combination with the promoter.

Examples of the host cells include mouse myeloma cells, rat myeloma cells, mouse hybridoma cells, Namalwa cells and Namalwa KJM-1 cells which are human cells, human embryonic kidney cells, human leukemia cells, African green monkey kidney cells, Chinese hamster-derived CHO cells, and HBT5637 (JP-A (Kokai) S63-299).

Mouse myeloma cells include SP2/0 and NS0; rat myeloma cells include YB2/0; human embryonic kidney cells include HEK293 (ATCC CRL-1573); human leukemia cells include BALL-1; and African green monkey kidney cells include COS-1 and COS-7.

As a method for introducing the recombinant DNA into animal cells, any method can be used so long as it will introduce the DNA into animal cells, and examples include the electroporation method [Cytotechnology, 3, 133 (1990)], the calcium phosphate method (JP-A (Kokai) H02-227075), the lipofection method [Proc. Natl. Acad. Sci. USA, 84, 7413 (1987)], and the method described in Virology, 52, 456 (1973).

In case of using an insect cell as the host, the protein can be produced by using, for example, methods described in Baculovirus Expression Vectors, A Laboratory Manual, W. H. Freeman and Company, New York (1992); Current Protocols in Molecular Biology; Molecular Biology, A Laboratory Manual; Bio/Technology, 6, 47 (1988), and such.

Specifically, a protein can be produced by cointroducing a recombinant gene transfer vector and a baculovirus into insect cells to obtain recombinant viruses in the culture supernatant of the insect cells, and then infecting insect cells with the recombinant viruses.

Examples of the gene transfer vectors used in this method include pVL1392, pVL1393, and pBlueBacIII (all manufactured by Invitrogen Corp.).

As baculovirus, for example, *Autographa californica* nuclear polyhedrosis virus which is a virus that infects the *Noctuidae Hadeninae* insects can be used.

As insect cells, ovarian cells of *Spodoptera frugiperda*, ovarian cells of *Trichoplusia ni*, cultured cells derived from silkworm ovary, and such can be used.

Ovarian cells of *Spodoptera frugiperda* include Sf9 and Sf21 (Baculovirus Expression Vectors, A Laboratory Manual); ovarian cells of *Trichoplusia ni* include High 5 and BTI-TN-5B1-4 (Invitrogen Corp.); and cultured cells derived from silkworm ovary include *Bombyx mori* N4.

Examples of a method for cointroducing the above-mentioned recombinant gene transfer vector and the above-mentioned baculovirus into insect cells for the preparation of recombinant viruses include the calcium phosphate method (JP-A (Kokai) H02-227075) and the lipofection method [Proc. Natl. Acad. Sci. USA, 84, 7413 (1987)].

In case of using a plant cell as the host cell, the Ti plasmid or tobacco mosaic virus vector can be used as the expression vector.

As a promoter, any promoter can be used so long as it will function in plant cells, and examples include the 35S promoter of cauliflower mosaic virus (CaMV) and the rice actin 1 promoter.

Examples of the host cells include plant cells of tobacco, potato, tomato, carrot, soybean, rape, alfalfa, rice, wheat, barley and such.

As a method for introducing the recombinant vector into plant cells, any method can be used so long as it will introduce the DNA into plant cells, and examples include methods using *Agrobacterium* (JP-A (Kokai) S59-140885, JP-A (Kokai) S60-70080, WO 94/00977), the electroporation method (JP-A (Kokai) S60-251887), and methods using a particle gun (gene gun) (Japanese Patent No. 2606856 and Japanese Patent No. 2517813).

6. Methods for Producing the Protein of the Present Invention

The proteins of the present invention can be produced by culturing the transformants obtained by the method of the above-described 5 in a medium, allowing the protein of the present invention to form and accumulate in the culture, and collecting the protein from the culture.

The host of the above-mentioned transformants for producing the protein of the present invention may be any host such as a bacterium, yeast, animal cell, insect cell, or plant cell, and it is preferably a bacterium, more preferably a microorganism belonging to the genus *Escherichia*, and even more preferably a microorganism belonging to *Escherichia coli*.

In case of expression using yeast, an animal cell, an insect cell, or a plant cell, proteins with sugars or sugar chains attached thereto can be obtained.

Methods for culturing the above-mentioned transformants in a medium can be carried out following general methods used for culturing the host.

As a medium for culturing transformants obtained by using prokaryotes such as *Escherichia coli* or eukaryotes such as yeast as the host, either of a natural medium and synthetic medium may be used, as long as it is a medium which contains carbon sources, nitrogen sources, inorganic salts, and such which can be assimilated by the organism and in which the transformants can be cultured efficiently.

As carbon sources, any carbon sources that can be assimilated by the organism can be used, and carbohydrates such as glucose, fructose, sucrose, molasses containing these, starch, or starch hydrolysate; organic acids such as acetic acid and propionic acid; and alcohols such as ethanol and propanol can be used.

As nitrogen sources, ammonia, ammonium salts of organic or inorganic acids such as ammonium chloride, ammonium sulfate, ammonium acetate, and ammonium phosphate, and other nitrogen-containing compounds, as well as peptone, meat extract, yeast extract, corn steep liquor, casein hydrolysate, soybean cake, soybean cake hydrolysate, and various fermentative microbial cells, and digestion products thereof can be used.

As inorganic salts, potassium dihydrogenphosphate, dipotassium hydrogenphosphate, magnesium phosphate, magnesium sulfate, sodium chloride, ferrous sulfate, manganese sulfate, copper sulfate, calcium carbonate, and such can be used.

Culturing is usually carried out under aerobic conditions, for example, by a shaking culture or a deep aeration agitation culture. The culturing temperature is preferably 15 to 40° C., and the culturing period is usually five hours to seven days. The pH is maintained at 3.0 to 9.0 during the culturing. The pH adjustment is carried out by using an organic or inorganic acid, an alkali solution, urea, calcium carbonate, ammonia, and such.

As necessary, antibiotics such as ampicillin and tetracycline can be added to the medium during the culturing.

When a microorganism transformed with an expression vector which uses an inducible promoter as the promoter is cultured, an inducer may be added to the medium as necessary. For example, when culturing a microorganism transformed with an expression vector which uses the lac promoter, isopropyl-β-D-thiogalactopyranoside or such may be added to the medium; and when culturing a microorganism transformed with an expression vector that uses the trp promoter, indoleacrylic acid or such may be added to the medium.

As medium for culturing the transformants obtained by using an animal cell as the host, generally used media can be used, such as the RPMI1640 medium [J. Am. Med. Assoc., 199, 519 (1967)], Eagle's MEM medium [Science, 122, 501 (1952)], DMEM medium [Virology, 8, 396 (1959)], and 199 medium [Proc. Soc. Biol. Med., 73, 1 (1950)], or media to which fetal calf serum or such has been added to these media.

Culturing is usually carried out for one to seven days under conditions of pH 6 to 8 at 25° C. to 40° C. in the presence of 5% $CO_2$ or the like.

As necessary, antibiotics such as kanamycin, penicillin, and streptomycin can be added to the medium during the culturing.

As a medium for culturing the transformants obtained by using an insect cell as the host, generally used media can be used, such as TNM-FH medium (manufactured by Pharmingen, Inc.), Sf-900 II SFM medium (manufactured by Life Technologies, Inc.), ExCell 400 and ExCell 405 (both manufactured by JRH Biosciences, Inc.), and Grace's Insect Medium [Nature, 195, 788 (1962)].

Culturing is usually carried out for one to five days under conditions of pH 6 to 7 at 25° C. to 30° C., and such.

As necessary, antibiotics such as gentamicin can be added to the medium during the culturing.

Transformants obtained by using a plant cell as the host can be cultured as cells or after differentiation into plant cells or plant organs. As medium for culturing the transformants, generally used media can be used, such as the Murashige and Skoog (MS) medium, White medium, and media to which plant hormones such as auxin and cytokinin have been added to these media.

Culturing is usually carried out for 3 to 60 days under conditions of pH 5 to 9 at 20° C. to 40° C.

As necessary, antibiotics such as kanamycin and hygromycin can be added to the medium during the culturing.

Methods for producing the proteins of the present invention include methods of production inside the host cells, methods of secretion outside the host cells, and methods of production on the host cell outer membrane. The structure of the protein to be produced can be altered according to the selected method.

When the protein of the present invention is produced in host cells or on the host cell outer membrane, the protein can be actively secreted outside the host cells by applying the method of Paulson, et al. [J. Biol. Chem., 264, 17619 (1989)], the method of Lowe, et al. [Proc. Natl. Acad. Sci. USA, 86, 8227 (1989); Genes Develop., 4, 1288 (1990)], or the methods described in JP-A (Kokai) H05-336963, WO 94/23021, and such.

Specifically, the protein of the present invention can be actively secreted outside the host cells by producing the protein in a form in which a signal peptide is added upstream of a protein containing the active site of the protein of the present invention by using genetic engineering techniques.

It is also possible to increase the production level by utilizing a gene amplification system which uses a dihydrofolate reductase gene or such according to the method described in JP-A (Kokai) H02-227075.

Furthermore, by redifferentiation of a gene-introduced animal or plant cell, a gene-introduced animal (non-human transgenic animal) or plant (transgenic plant) can be constructed, and this can be used to produce the proteins of the present invention.

When the transformant producing the protein of the present invention is an animal or a plant, the protein can be produced by rearing or culturing the animal or plant according to general methods, allowing the protein to form and accumulate, and collecting the protein from the animal or plant.

Methods for producing the protein of the present invention using an animal include, for example, methods of producing the protein of the present invention in an animal constructed by gene introduction according to known methods [Am. J. Clin. Nutr., 63, 639S (1996); Am. J. Clin. Nutr., 63, 627S (1996); Bio/Technology, 9, 830 (1991)].

In the case of an animal, the protein of the present invention can be produced, for example, by rearing a non-human transgenic animal into which the DNA of the present invention or the DNA for use in the production method of the present invention has been introduced, allowing the protein to form and accumulate in the animal, and recovering the protein from the animal. The places where the protein is formed and accumulated in the animal include milk (JP-A (Kokai) S63-309192), egg, and such of the animal. As promoter used in this process, any promoter can be used so long as it will function in the animal, and for example, mammary gland cell-specific promoters such as a casein promoter, β casein promoter, β lactoglobulin promoter, and whey acidic protein promoter can be suitably used.

Methods for producing the protein of the present invention using a plant include, for example, methods for producing the protein by cultivating a transgenic plant into which the DNA encoding the protein of the present invention has been introduced according to known methods [Soshiki Baiyo (Tissue Culture), 20 (1994); Soshiki Baiyo, 21 (1995); Trends Biotechnol., 15, 45 (1997)], allowing the protein to form and accumulate in the plant, and collecting the protein from the plant.

As a method for isolating/purifying the protein of the present invention produced by using the transformant that produces the protein of the present invention, general methods for isolating and purifying enzymes can be used.

For example, when the protein of the present invention is produced in a soluble state in cells, the cells are collected by centrifugation after completion of culturing, suspended in an aqueous buffer, then disrupted using a sonicator, French press, Manton Gaulin homogenizer, Dynomill, or such to obtain a cell-free extract.

A purified preparation can be obtained from the supernatant obtained by centrifugation of the cell-free extract by using, alone or in combination, general methods for isolating and purifying enzymes. The general methods include a solvent extraction, a salting-out using ammonium sulfate or such, a desalting, a precipitation using an organic solvent, an anion exchange chromatography using resins such as diethylaminoethyl (DEAE)-Sepharose or DIAION HPA-75 (manufactured by Mitsubishi Kasei Corp.), a cation exchange chromatography using resins such as S-Sepharose FF (manufactured by GE Healthcare Biosciences), a hydrophobic chromatography using resins such as butyl Sepharose and phenyl Sepharose, a gel filtration using a molecular sieve, an affinity chromatography, a chromatofocusing, and an electrophoresis such as isoelectric focusing.

When the protein is produced in the form of an insoluble body in cells, the cells are similarly collected and disrupted, centrifuged to obtain a precipitate fraction, and after the protein is recovered from the precipitate fraction by an ordinary method, the insoluble body of the protein is solubilized using a protein-denaturing agent.

A purified preparation can be obtained by diluting or dialyzing the solubilized solution with a solution containing no protein-denaturing agent or a solution containing a protein-denaturing agent at such a low concentration that the protein is not denatured, constituting the protein to have a normal three-dimensional structure, then isolating and purifying the protein using methods similar to those described above.

When the protein of the present invention or its derivative such as a sugar-modified form is extracellularly secreted, the protein or its derivative such as a sugar-added form can be recovered in the culture supernatant.

Specifically, the culture is treated by similar means as described above such as centrifugation to obtain a soluble fraction, and a purified preparation can be obtained from the soluble fraction by using isolation and purification methods similar to those described above.

An example of a protein obtained in the above manner includes a protein comprising the amino acid sequence represented by SEQ ID NO: 1.

Further, the protein of the present invention can be produced as a fusion protein with another protein and purified by utilizing affinity chromatography using a substance having affinity for the fused protein. For example, the protein of the present invention can be produced as a fusion protein with protein A according to the method of Lowe, et al. [Proc. Natl. Acad. Sci. USA, 86, 8227 (1989); Genes Develop., 4, 1288 (1990)] or methods described in JP-A (Kokai) H05-336963 and WO 94/23021, and purified by affinity chromatography using immunoglobulin G.

The protein of the present invention can also be produced as a fusion protein with a Flag peptide and purified by affinity chromatography using an anti-Flag antibody [Proc. Natl. Acad. Sci. USA, 86, 8227 (1989); Genes Develop., 4, 1288 (1990)], or it can be produced as a fusion protein with polyhistidine and purified by affinity chromatography using a metal-coordinated resin having high affinity to polyhistidine. Further, the protein can be purified by affinity chromatography using an antibody against the protein itself.

The protein of the present invention can be produced by chemical synthesis methods such as the Fmoc method (the fluorenylmethyloxycarbonyl method) and the tBoc method (the t-butyloxycarbonyl method) based on the amino acid sequence information on a protein obtained above. Further, the protein can be chemically synthesized by using peptide synthesizers from Advanced ChemTech, Perkin-Elmer, Pharmacia, Protein Technology Instrument, Synthecell-Vega, PerSeptive, Shimadzu Corporation, and such.

7. Methods for Measuring Glycated Proteins Using the Proteins of the Present Invention The proteins of the present invention have the characteristic of producing hydrogen peroxide by acting on glycated peptides produced from glycated proteins following the action of a protease on the glycated proteins; therefore, they can be used to measure glycated proteins in various types of samples. Specifically, glycated proteins in a sample can be measured by reacting the sample with a protease to produce glycated peptides, reacting the produced glycated peptides with the protein of the present invention, and measuring a substance produced by the reaction between the glycated peptides and the protein of the present invention or a substance consumed in the reaction between the glycated peptides and the protein of the present invention. The reactions relating to measurement of the glycated proteins in the sample can be carried out in the aqueous media described below. A glycated protein in the present invention is, for example, glycated hemoglobin such as hemoglobin A1c or glycated albumin; it is preferably glycated hemoglobin, and particularly preferably hemoglobin A1c.

The measurement methods of the present invention are described below.

Samples and Objects to be Measured

The samples used in the measurement methods of the present invention are not particularly limited so long as they contain a glycated protein, and examples include biological samples such as whole blood, plasma, serum, blood cells, cell samples, urine, spinal fluid, sweat, tear fluid, saliva, skin, mucous membrane, and hair, as well as food. As samples, whole blood, plasma, serum, blood cells and such are preferred, and whole blood, blood cells, and such are particularly preferred. Whole blood includes samples of whole blood-derived blood cell fractions admixed with plasma. With regard to these samples, samples subjected to pretreatments such as hemolysis, separation, dilution, concentration, and purification can be used.

Hemoglobin is a tetramer consisting of two polypeptides of the α-chain and the β-chain, and has a molecular weight of 64,500. The sequence of the three amino acids at the N terminus of the α-chain of hemoglobin is valine-leucine-serine and the sequence of the three amino acids at the N terminus of the β-chain is valine-histidine-leucine. Hemoglobin A1c is defined as a hemoglobin in which the N-terminal valine of the β-chain is glycated. Furthermore, hemoglobin is known to have multiple glycation sites within the molecule (The Journal of Biological Chemistry (1980), 256, 3120-3127).

By making a protease act on a sample containing glycated hemoglobin, glycated amino acids and/or glycated oligopeptides are produced, such as α-fructosyl valine (hereinafter, abbreviated as α-FV) and α-FVH which are derived from glycated hemoglobin in which the β-chain N-terminal valine residue is glycated, α-FV and α-fructosyl valyl leucine (hereinafter, abbreviated as α-FVL) which are derived from glycated hemoglobin in which the α-chain N-terminal valine residue is glycated, and ε-FK derived from glycation of the ε-amino group of lysine residues inside the α-chain and/or β-chain.

Furthermore, when the sample is whole blood, glycated amino acids such as ε-FK are also produced from glycated proteins in the whole blood other than glycated hemoglobin, such as glycated albumin.

Thus, when a protease is made to act on a sample containing purified hemoglobin or a sample containing whole blood, for example, α-FVH, α-FV, ε-FK, and α-FVL are produced, where α-FVH and α-FVL are derived from glycated hemoglobin and α-FVH is specifically derived from hemoglobin A1c.

Therefore, when measuring hemoglobin A1c, one can specifically measure α-FVH. The proteins of the present invention are highly reactive towards α-FVH, and have low reactivity towards ε-FK; accordingly, hemoglobin A1c can be measured effectively.

The Proteases

As proteases that can be used in the present invention, any protease can be used so long as it will act on the glycated protein to be measured included in the sample, and examples include proteases derived from animals, plants, and microorganisms, metalloproteases, endoproteases, exoproteases, serine proteases, cysteine proteases, acidic proteases, alkaline proteases, and thiol proteases.

Examples of animal-derived proteases include elastase, trypsin, chymotrypsin, pepsin, bovine pancreatic protease, pig liver-derived leucine aminopeptidase, cathepsin, calpain, protease type I, protease type XX (the above are manufactured by Sigma), aminopeptidase M, carboxypeptidase A (the above are manufactured by Boehringer Mannheim), and pancreatin (manufactured by Wako Pure Chemical Industries Ltd. and Sigma).

Examples of plant-derived proteases include kallikrein, ficin, papain, chymopapain, bromelain, carboxypeptidase W (the above are manufactured by Sigma), papain W-40, and bromelain F (the above are manufactured by Amano Enzyme Inc.).

Examples of microorganism-derived proteases include the following (1) to (14).

(1) *Bacillus*-derived proteases: Subtilisin, Protease type-VIII, Protease type-IX, Protease type-X, Protease type-XV, Protease type-XXIV, Protease type-XXVII, Protease type-XXXI, Proteinase type-WI, *Bacillus licheniformis*-derived protease (the above are manufactured by Sigma), thermolysin (manufactured by Wako Pure Chemical Industries), Orientase-90N, Orientase-10NL, Orientase-22BF, Orientase Y, Orientase-SBL, Nucleisin (the above are manufactured by HBI Enzymes Inc.), Proleather FG-F, Protease NL "Amano", Protease S "Amano" G, Protease N "Amano" G (the above are manufactured by Amano Enzyme Inc.), GODO-BNP, GODO-BAP, GODO high-purity protease (the above are manufactured by GODO SHUSEI), Protin-AC10F, Protin-NL10, Protin-NC25, Protin-NY10, Protin-PC10F, Protin-PS10, Deskin, Depirays, Biosoke, Thermoase-PC10F, thermolysin (the above are manufactured by Daiwa Kasei), Toyozyme NEP, neutral protease (the above are manufactured by Toyobo Co.), Neutrase, Esperase, Savinase, Dyrazym, Bio-Feed Pro, Alcalase, NUE, Pyrase, Clear Lens-Pro, Evelase, Novozyme-FM, volan (the above are manufactured by Novo Nordisk Bioindustry), Enzylon-NBS, Enzylon-SA (the above are manufactured by Rakuto Chemical Industry), Nagarse, Biopullase APL-30, Biopullase SP-4FG, Biopullase XL-416F, Biopullase $A_L$-15FG, Pectinase XP-534 (the above are manufactured by Nagase ChemteX Corp.), Aroase $A_P$-10, Protease YB (the above are manufactured by Yakult Pharmaceutical Industry Co.), Colorase-N, Colorase-7089, Belon W (the above are manufactured by Higuchi Shokai), Chirazyme P-1, Dispase (the above are manufactured by Roche), Satilysin (manufactured by Boehringer Mannheim), Proteinase N, Proteinase Bacterial Subtilisin (the above are manufactured by Fluka), Pronase E (manufactured by Kaken Pharmaceutical Co.), and such.

(2) *Aspergillus*-derived proteases: Protease type-XIII, -XIX, -XXIII (the above are manufactured by Sigma), Sumizyme-MP, Sumizyme-AP, Sumizyme-LP L, Sumizyme-LP20, Sumizyme-FP, Enzyme P-3 (the above are manufactured by SHINNIHON CHEMICALS Co.), Orientase-20A, Orientase-ONS, Orientase-ON5, Tetrase S (the above are manufactured by HBI Enzymes Inc.), Umamizyme G, Neurase A, Neurase F3G, Protease-A "Amano" G, Protease K "Amano", Protease M "Amano" G, Protease P "Amano" 3G (the above are manufactured by Amano Enzyme Inc.), alkaline protease, acidic protease, Morsin, AO Protease, peptidase (the above are manufactured by Kikkoman), Protin-F, Protin-FN, Protin-FA (the above are manufactured by Daiwa Kasei), Denapsin 2P, Denazyme-SA-7, Denazyme-AP, Denazyme A$_P$ (the above are manufactured by Nagase ChemteX Corp.), Protease YP-SS, Pantidase-NP-2, Pantidase-P (the above are manufactured by Yakult Pharmaceutical Industry Co.), Sakanase (manufactured by Kaken Pharmaceutical Co.), Flavorzyme (manufactured by Novo Nordisk Bioindustry), Belon PS (manufactured by Higuchi Shokai), Proteinase 6 (manufactured by Fluka), Protease A5 (manufactured by Kyowa Kasei), and such.

(3) *Rhizopus*-derived proteases: Protease Type-XVIII (manufactured by Sigma), Peptidase R, Neurase F (the above are manufactured by Amano Enzyme Inc.), XP-415 (manufactured by Nagase ChemteX Corp.), and such.

(4) *Penicillium*-derived proteases: PD enzyme (manufactured by Kikkoman Corp.), Protease B "Amano" (manufactured by Amano Enzyme Inc.), Deoxin 1 (manufactured by Nagase ChemteX Corp.), and such.

(5) *Streptomyces*-derived proteases: Protease Type-XIV (also called Pronase), Protease-XXI (the above are manufactured by Sigma), Actinase-AS, Actinase-AF, Actinase-E (the above are manufactured by Kaken Pharmaceutical Co.), Alkalofilic Proteinase (manufactured by Toyobo Co.), Pronase E (manufactured by Roche, Calbiochem-Novabiochem, and Sigma), Pronase (manufactured by Boehringer Mannheim), and such.

(6) *Staphylococcus*-derived proteases: Protease-Type XVII (manufactured by Sigma), Endoproteinase Glu-C (manufactured by Boehringer Mannheim), V8 Protease (manufactured by TAKARA, and Wako Pure Chemical Industries Ltd.), and such.

(7) *Clostridium*-derived proteases: Clostripain, Non-specific Neutral Protease, Collagenase Type 1A (the above are manufactured by Sigma), and such.

(8) *Lysobacter*-derived proteases: Endoproteinase Lys-C (manufactured by Sigma), and such.

(9) *Grifola*-derived proteases: Metalloendopeptidase (manufactured by Sigma).

(10) Yeast-derived proteases: Proteinase A (manufactured by Sigma), Carboxypeptidase Y (manufactured by Boehringer Mannheim), and such.

(11) *Tritirachium*-derived proteases: Proteinase K (manufactured by Sigma, Roche, and Wako Pure Chemical Industries), and such.

(12) *Thermus*-derived proteases: Aminopeptidase T (manufactured by Boehringer Mannheim), and such.

(13) *Pseudomonas*-derived proteases: Endoproteinase Asp-N (manufactured by Wako Pure Chemical Industries), and such.

(14) *Achromobacter*-derived proteases: Lysylendopeptidase, Achromopeptidase (the above are manufactured by Wako Pure Chemicals), AP-1 (manufactured by TAKARA), and such.

In the measurement methods of the present invention, proteases derived from *Bacillus, Aspergillus, Streptomyces*, and *Tritirachium* are preferred since they have large effects on human hemoglobin, and *Bacillus*-derived proteases are particularly preferred.

Examples of metalloproteases include thermolysin and protease N. Examples of endoproteases include thermolysin, papain, subtilisin, pepsin, trypsin, and chymotrypsin. Examples of exoproteases include amino peptidase and carboxypeptidase. Examples of serine proteases include thermitase, proteinase K, trypsin, chymotrypsin, thrombin, plasmin, and elastase. Examples of cysteine proteases include papain and caspase. Examples of acidic proteases include pepsin and cathepsin D. Examples of alkaline protease include Orientase 22BF. Examples of thiol proteases include papain, ficin, and bromelain.

The protease concentration is preferably 0.01 U/mL to 100,000 U/mL and more preferably 0.1 U/mL to 10,000 U/mL in the reaction solution. Furthermore, two or more types of enzymes can be used in combination in the present invention.

A protease used in the present invention is preferably uncolored, and for example, the absorbance at the wavelengths of 300 nm to 800 nm of a 1,000 U/mL aqueous solution of the protease is preferably 100 mAbs or less, and more preferably 0 to 10 mAbs. As protease, a protease purified by various types of chromatography, salting-out, dialysis, activated carbon treatment, and such, and whose above-described absorbance has been decreased is preferred.

In the measurement methods of the present invention, the concentration of the enzyme, a protein of the present invention, is preferably 0.01 U/mL to 1,000 U/mL and more preferably 0.1 U/mL to 100 U/mL in the reaction solution.

Measurement Methods

Glycated protein to be measured in a sample of the present invention can be measured by sequentially carrying out the following steps (i) to (iii):
(i) producing a glycated peptide by reacting a sample with a protease;
(ii) reacting the formed glycated peptide with the protein of the present invention; and
(iii) measuring a substance formed or consumed in step (ii).

The above-mentioned steps (i) to (iii) can be carried out in an aqueous medium. Examples of the aqueous medium include deionized water, distilled water, and buffer solution; and, a buffer solution is preferred. Examples of buffer agents to be used in the buffer solution include tris(hydroxymethyl)aminomethane buffer (Tris buffer), phosphate buffer, borate buffer, and Good's buffer.

Examples of Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxy-3-propanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]-glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO) and N-cyclohexyl-3-aminopropanesulfonic acid (CAPS).

The concentration of the buffer is not particularly limited as long as it is suitable for measurement, but the concentration is preferably 0.001 mol/L to 2.0 mol/L, and more preferably 0.005 mol/L to 1.0 mol/L.

For the reactions in each step, the reaction temperature is for example, 10° C. to 50° C. and preferably 20° C. to 40° C., and the reaction time is 1 second to 60 minutes and preferably 1 to 10 minutes.

The protease does not have to be particularly inactivated after performing step (i) if it does not affect the reaction of step (ii); however, heating, cooling, centrifugation, membrane filtration, addition of an inhibitor, or such can be carried out so that the enzyme will not act in step (ii).

In step (ii), products formed in the reaction solution due to the reaction between the glycated peptide and the protein of the present invention having fructosyl peptide oxidase activity include hydrogen peroxide, sugar osone (α-keto aldehyde), and peptides. Furthermore, in step (ii), a substance consumed by the reaction between the glycated peptide and the protein of the present invention having fructosyl peptide oxidase activity is, for example, an oxygen molecule. Oxygen molecules consumed in step (ii) are measured, for example, by electrochemical measurement methods using an oxygen electrode.

Hydrogen peroxide produced in step (ii) of the present invention can be measured using, for example, optical techniques or electrochemical techniques. Examples of optical techniques include absorbance methods and luminescence methods. Specific examples include optical determination using a reagent for measuring hydrogen peroxide and electrochemical determination using a hydrogen peroxide electrode.

A reagent for measuring hydrogen peroxide is a reagent for converting the produced hydrogen peroxide into a detectable substance. Examples of the detectable substance include dye and light; and, a dye is preferred.

When the detectable substance is dye, the reagent for measuring hydrogen peroxide includes peroxidative active substances such as peroxidase and oxidative coloring chromogens. Examples of the oxidative coloring chromogens include oxidative coupling-type chromogens and leuco-type chromogens which are described later.

When the detectable substance is light, the reagent for measuring hydrogen peroxide includes chemiluminescent substances. Bioluminescent substances are included in chemiluminescent substances, and examples include luminol, isoluminol, lucigenin, acridinium ester, and oxalate ester.

When using a reagent containing a peroxidative active substance such as peroxidase and an oxidative coloring chromogen as reagent for measuring hydrogen peroxide, hydrogen peroxide can be measured by reacting hydrogen peroxide with the oxidative coloring chromogen in the presence of a peroxidative active substance to form a dye and then measuring the formed dye. Furthermore, when using a reagent for measuring hydrogen peroxide which contains a chemiluminescent substance, hydrogen peroxide can be measured by reacting hydrogen peroxide with a chemiluminescent substance to form photons and then measuring the formed photons.

An oxidative coupling-type chromogen is a chromogen which reacts with hydrogen peroxide in the presence of a peroxidative active substance such as peroxidase to produce a dye by an oxidative coupling reaction. Specific examples of the oxidative coupling-type chromogen include couplers such as 4-aminoantipyrine, and phenolic or anilinic hydrogen donors. A coupler and a phenolic or anilinic hydrogen donor compound undergo oxidative coupling in the presence of hydrogen peroxide and a peroxidative active substance to produce a dye.

Examples of a coupler include 4-aminoantipyrine (4-AA) and 3-methyl-2-benzothiazolinone hydrazone.

Examples of a phenolic hydrogen donor include phenol, 4-chlorophenol, 3-methylphenol, and 3-hydroxy-2,4,6-triiodobenzoic acid (HTIB).

Examples of an anilinic hydrogen donor include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, N-ethyl-N-(2-hydroxy-3-sulfopropyl)-4-fluoro-3,5-dimethoxyaniline (F-DAOS), N-[2-(succinylamino)ethyl]-2-methoxy-5-methylaniline (MASE), and N-ethyl-N-[2-(succinylamino)ethyl]-2-methoxy-5-methylaniline (Et-MASE).

Leuco-type chromogen is a chromogen which produces a dye by itself by reacting with hydrogen peroxide in the presence of a peroxidative active substance such as peroxidase. Specific examples include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino)diphenylamine sodium salt (DA-64), 10-(carboxymethylaminocarbonyl)-3,7-bis(dimethylamino)phenothiazine sodium salt (DA-67), 4,4'-bis(dimethylamino)diphenylamine, bis[3-bis(4-chlorophenyl)methyl-4-dimethylaminophenyl]amine (BCMA), N,N,N',N',N'',N''-hexa-3-sulfopropyl-4,4',4''-triaminotriphenylmethane (TPM-PS), diaminobentidine, hydroxyphenylpropionic acid, tetramethylbentidine, and orthophenylenediamine.

In the measurement of hydrogen peroxide, the concentration of the peroxidative active substance is not particularly limited as long as it is suitable for measurement; and, when peroxidase is used as the peroxidative active substance, the concentration is preferably 1 U/mL to 100 U/mL and more preferably 2 U/mL to 50 U/mL. The concentration of the oxidative coloring chromogen is not particularly limited as long as it is suitable for measurement; and, it is preferably 0.01 g/L to 10 g/L and more preferably 0.02 g/L to 5 g/L.

When hydrogen peroxide is measured using a hydrogen peroxide electrode, the electrode to be used is not particularly limited as long as it is a material that allows transfer of electrons with the hydrogen peroxide, and examples include platinum, gold and silver. As method for measurement, known methods such as amperometry, potentiometry, and coulometry can be used. By interposing an electron-transfer substance in the reaction between the electrode and the oxidase or substrate, the resulting oxidation or reduction current or its electrical quantity can also be measured.

Any substance having a function of transferring electrons can be used as the electron-transfer substance, and examples include substances such as ferrocene derivatives and quinone derivatives. Furthermore, by interposing an electron-transfer substance between the electrode and the hydrogen peroxide produced by the oxidase reaction, the resulting oxidation or reduction current or its electrical quantity can be measured.

In step (ii), a sugar osone (an α-keto aldehyde) is produced together with hydrogen peroxide; therefore, hemoglobin A1c in a sample can also be measured by measuring the produced sugar osone (an α-keto aldehyde). By letting glucose oxidase act on the α-keto aldehyde and by measuring the produced hydrogen peroxide as well, highly sensitive measurements can be taken (JP-A (Kokai) 2000-333696).

Methods for Preparing Samples

Samples containing the glycated protein to be measured can be separated from biological samples as necessary. Separation methods include centrifugation, filtration, and methods using blood cell separation membrane. For example, a method of separation by centrifugation can separate whole blood into blood cells and plasma or serum. As necessary, the blood cells can be washed with an isotonic solution such as physiological saline solution to obtain washed blood cells from which plasma-derived components have been removed.

When using blood cells as samples, hemolysis can be carried out by diluting a sample containing blood cells such as whole blood, blood cells, or washed blood cells using a hypotonic solution. Any hypotonic solution can be used so long as it can cause hemolysis of blood cells; examples include water and buffer, and the hypotonic solution preferably contains an additive such as a surfactant. Examples of surfactant include nonionic surfactant, cationic surfactant, anionic surfactant, and amphoteric surfactant.

Methods for preparing washed blood cells include the following method.

Blood is collected from healthy individuals and diabetes patients, mixed by overturning, and then subjected to centrifugation (3,000 rpm) at 25° C. for five minutes. After centrifugation, the supernatant plasma is removed. For one part of the lower-part blood cell layer, four parts of physiological saline solution is added, this is mixed by overturning and subjected to centrifugation (3,000 rpm) at 25° C. for five minutes. After centrifugation, the supernatant physiological saline solution is removed. After repeating this washing operation three times, nine parts of distilled water is added to one part of the washed blood cell layer, and this yields washed blood cells.

Reagents and Kits for Measuring Glycated Proteins

The reagents for measuring glycated proteins and kits for measuring glycated proteins of the present invention can be used in the methods for measuring glycated proteins of the present invention. The reagents for measuring glycated proteins of the present invention can take the form of a kit, as a form suitable for storage, transport, and distribution. Examples of the form of the kit include a two-reagent system and a three-reagent system.

The reagents of the present invention for measuring glycated proteins include proteases as well as the proteins of the present invention having fructosyl peptide oxidase activity. Furthermore, the reagents for measuring glycated proteins of the present invention can include reagents for measuring a product formed by the reaction between the protein of the present invention and a glycated peptide produced from a glycated protein. Examples of a product formed by the reaction between the protein of the present invention and a glycated peptide produced from a glycated protein include hydrogen peroxide, sugar osone (an α-keto aldehyde), and peptides. Examples of reagents for measuring a product formed by the reaction between the protein of the present invention and a glycated peptide produced from a glycated protein include reagents for measuring hydrogen peroxide, reagents for measuring a sugar osone (an α-keto aldehyde), and reagents for measuring a peptide (Val-His); and, reagents for measuring hydrogen peroxide are preferred.

Examples of kits of the present invention for measuring glycated proteins to be measured include the kits of the following embodiments:

Kit 1 (two-reagent-system kit)

A kit comprising the following two reagents:

(1) a reagent comprising a protease; and (2) a reagent comprising the protein of the present invention.

Kit 2 (two-reagent-system kit)

A kit comprising the following two reagents:

(1) a reagent comprising a protease; and (2) a reagent comprising a protein of the present invention and a reagent for measuring a product formed by the reaction between the protein of the present invention and a glycated peptide produced from a glycated protein.

Kit 3 (two-reagent-system kit)

A kit comprising the following two reagents:

(1) a reagent comprising a protease and a reagent for measuring a product formed by the reaction between the protein of the present invention and a glycated peptide produced from a glycated protein; and (2) a reagent comprising the protein of the present invention.

Kit 4 (two-reagent-system kit)

A kit comprising the following two reagents:

(1) a reagent comprising a protease and a reagent for measuring a product formed by the reaction between the protein of the present invention and a glycated peptide produced from a glycated protein; and (2) a reagent comprising the protein of the present invention and a reagent for measuring a product formed by the reaction between the protein of the present invention and a glycated peptide produced from a glycated protein.

Kit 5 (three-reagent-system kit)

A kit comprising the following three reagents:

(1) a reagent comprising a protease;

(2) a reagent comprising the protein of the present invention; and (3) a reagent comprising a reagent for measuring a product formed by the reaction between the protein of the present invention and a glycated peptide produced from a glycated protein.

Kit 6 (three-reagent-system kit)

A kit comprising the following three reagents:

(1) a reagent comprising a protease and a reagent for measuring a product formed by the reaction between the protein of the present invention and a glycated peptide produced from a glycated protein;

(2) a reagent comprising the protein of the present invention; and (3) a reagent comprising a reagent for measuring a product formed by the reaction between the protein of the present invention and a glycated peptide produced from a glycated protein.

Kit 7 (three-reagent-system kit)

A kit comprising the following three reagents:

(1) a reagent comprising a protease;

(2) a reagent comprising the protein of the present invention and a reagent for measuring a product formed by the reaction between the protein of the present invention and a glycated peptide produced from a glycated protein; and (3) a reagent comprising a reagent for measuring a product formed by the reaction between the protein of the present invention and a glycated peptide produced from a glycated protein.

Kit 8 (three-reagent-system kit)

A kit comprising the following three reagents:

(1) a reagent comprising a protease and a reagent for measuring a product formed by the reaction between the protein of the present invention and a glycated peptide produced from a glycated protein;

(2) a reagent comprising the protein of the present invention and a reagent for measuring a product formed by the reaction between the protein of the present invention and a glycated peptide produced from a glycated protein; and (3) a reagent comprising a reagent for measuring a product formed by the reaction between the protein of the present invention and a glycated peptide produced from a glycated protein.

Examples of each of the protease, the protein of the present invention, the glycated protein, and the reagent for measuring a product formed by the reaction between a protein of the present invention and a glycated peptide produced from a glycated protein used in the reagents and kits for measurement of the present invention include those mentioned above.

When the reagent for measuring a product formed by the reaction between the protein of the present invention and a glycated peptide produced from a glycated protein is a reagent for measuring hydrogen peroxide, examples of the reagent for measuring hydrogen peroxide include the aforementioned reagents for measuring hydrogen peroxide. When an oxidative coupling-type chromogen is used as the reagent for measuring hydrogen peroxide, a coupler and a phenolic or anilinic hydrogen donor can be included in the same reagent; and, they are preferably included in separate reagents.

The reagents for measurement and kits for measurement of the present invention can further comprise standard for measurement such as standard proteins.

As necessary, the reagents for measurement and kits for measurement of the present invention can contain buffers, stabilizers, preservatives, agents for removing affecting substances, agents for suppressing nonspecific reaction, surfactants, and such. Examples of buffers include the aforementioned buffers. Examples of stabilizers include ethylenediaminetetraacetic acid (EDTA), sucrose, calcium chloride, amino acids, albumin, dextran, and salts such as calcium acetate. Examples of preservatives include sodium azide and antibiotics. Examples of agents for removing affecting substances include ascorbate oxidase for eliminating the effect of ascorbic acid. Examples of agents for suppressing nonspecific reaction include polymeric compounds such as dextran sulfate. Examples of surfactants include nonionic surfactants, cationic surfactants, anionic surfactants, and zwitterionic surfactants.

The reagents and kits for measurement of the present invention can be in a freeze-dried state or in a state dissolved in a reaction solution. When using a kit in a freeze-dried state, the kit can be used after dissolution in an aforementioned aqueous medium or reaction solution. When using a kit in a freeze-dried state, reagents for dissolving the freeze-dried reagent or such can be included in the kit, as necessary.

The protease content in the kit for measurement of the present invention is preferably a content which will give a concentration of 0.01 U/mL to 1,000,000 U/mL, more preferably a concentration of 0.1 U/mL to 100,000 U/mL in a state dissolved in an aqueous medium.

The content of the protein of the present invention in the kit for measurement of the present invention is preferably a content which will give a concentration of 0.01 U/mL to 10,000 U/mL, more preferably a concentration of 0.1 U/mL to 1,000 U/mL in a state dissolved in an aqueous medium.

The contents of peroxidase and an oxidative coupling-type chromogen in a kit, when a reagent containing peroxidase and an oxidative coupling-type chromogen is used as the reagent for measuring hydrogen peroxide, are preferably contents which will give concentrations of 1 U/mL to 600 U/mL and 0.5 g/L to 40 g/L, respectively, and more preferably concentrations of 2 U/mL to 150 U/mL and 1 g/L to 20 g/L, respectively, in a state dissolved in an aqueous medium.

All prior art references cited herein are incorporated by reference into this description.

EXAMPLES

Herein below, Examples are indicated, but the present invention is not to be construed as being limited thereto.

Example 1

Construction of an Expression System for the Fructosyl Peptide Oxidase Gene

The *Emericella nidulans* KY125 strain was selected as the fungus for producing an enzyme with relatively high activity towards α-FVH and low activity towards ε-FK.

Next, the full length of a fructosyl peptide oxidase gene was amplified by the PCR method using primers (SEQ ID NOs: 5 and 6) prepared by referring to the DNA sequence of *Aspergillus nidulans* FGSC A4 strain (Nature, 438, 1105 (2005)) which is a fungus related to *E. nidulans* and whose complete genomic sequence has been decoded. When this DNA sequence was decoded using a DNA sequencer, the fructosyl peptide oxidase gene of the KY125 strain contained five introns between six exons. The exon portions alone were amplified by the overlapping PCR method (Nucleic Acids Res., 16, 7351 (1988)), and these were linked to construct a mature-form fructosyl peptide oxidase gene consisting only of exons. By decoding this DNA sequence, the mature-form fructosyl peptide oxidase gene was found to consist of 1317 bp and 438 amino acids.

To construct a system for expressing the fructosyl peptide oxidase gene of the *E. nidulans* KY125 strain, the fructosyl peptide oxidase gene obtained above was inserted into the NcoI and BamHI restriction enzyme sites of the pTrc99A expression vector (4,176-bp, manufactured by GE Japan). *E. coli* XL1-Blue (manufactured by Funakoshi Corp.) was transformed using this recombinant DNA (plasmid) (pTrcFPOX-1). By culturing this transformant overnight in LB medium containing 50 mg/L of ampicillin, a protein having fructosyl peptide oxidase activity was obtained in these bacteria.

Example 2

Construction of Fructosyl Oxide Peptidase

Random mutations were introduced into the fructosyl peptide oxidase gene obtained in Example 1. Introduction of random mutations was carried out using the GeneMorph II Random Mutagenesis Kit from Stratagene. Introduction of nucleotide substitutions and full-length amplification were carried out simultaneously by a PCR method using pTrcF-POX-1 as the template DNA and primers (SEQ ID NOs: 5 and 6) that corresponds to the regions corresponding to the 5'-side upstream portion and the 3'-side downstream portion of the fructosyl peptide oxidase gene.

The PCR product was cleaved using NcoI and BamHI, then purified using a PureLink PCR Purification Kit (Invitrogen Corp.), ligated into the NcoI and BamHI sites of pTrc99A, and then this was used to transform the *E. coli* XL1-Blue strain.

Colonies (transformants) that grew when cultured overnight on a plate containing an LB medium containing 50 mg/L of ampicillin were picked. They were cultured at 30° C. for 18 hours using a 24-well culture plate (manufactured by Sumitomo Bakelite Co.) containing 2 mL of the LB medium containing 50 mg/L of ampicillin BugBuster (manufactured by Novagen) was added to the medium, and after bacterial cell lysis and centrifugation, the enzyme activity towards two types of substrates (ε-FK and α-FVH) was measured using this supernatant solution as the enzyme source.

Meanwhile, plasmids were prepared from each transformant, and the nucleotide sequence of the fructosyl peptide oxidase gene portion was decoded using a DNA sequencer. Then, changes in enzyme activity, heat resistance, and substrate specificity were correlated with the changes in the nucleotide sequence (amino acid sequence).

In this context, as a fructosyl peptide oxidase with increased α-FVH activity or heat resistance, a fructosyl peptide oxidase (hereinafter referred to as FPOX-9) with substitutions of Ser at position 71 to Tyr, Lys at position 109 to Arg, Ile at position 94 to Met, Phe at position 269 to Ile, and Glu at position 104 to Lys in the fructosyl peptide oxidase obtained in Example 1 was obtained. The amino acid sequence of FPOX-9 is shown in SEQ ID NO: 1, and the nucleotide sequence encoding this amino acid sequence is shown in SEQ ID NO: 2.

Next, FPOX-10 produced by substituting Ser at position 59 in FPOX-9 to Gly, FPOX-11 produced by substituting Met at position 58 and Gly at position 105 in FPOX-10 to Phe and Lys respectively, FPOX-13 produced by substituting Gly at position 183 in FPOX-11 to Glu, and FPOX-14 produced by substituting Pro at position 302 in FPOX-13 to Leu were obtained. Furthermore, FPOX-15 produced by substituting Asn at position 272 in FPOX-14 to Asp was obtained. The amino acid sequence of FPOX-15 and the nucleotide sequence encoding this amino acid sequence are shown in SEQ ID NO: 3 and SEQ ID NO: 4, respectively.

As substitutions accumulated from these operations, activity towards α-FVH increased sequentially as shown in Table 1. The α-FVH activity of FPOX-15 was increased to approximately four times that of FPOX-9. In contrast, the activity of FPOX-15 towards ε-FK decreased to approximately 70% that of FPOX-9. Therefore, the α-FVH/ε-FK ratio of FPOX-15 became approximately 7.3 and the value increased approximately 5.6 times compared to the value of FPOX-9. Furthermore, FPOX-15 retained approximately 80% of the enzyme activity even after heat treatment at 50° C. for 15 minutes, so that thermostability had also greatly increased.

TABLE 1

| No. | FPOX | NUMBER OF ADDED MUTATIONS | RELATIVE ACTIVITY α-FVH | RELATIVE ACTIVITY ε-FK | FVH/FK | HEAT RESISTANCE (50° C., 15 minutes) |
|---|---|---|---|---|---|---|
| 1 | FPOX-9 | 0 | 1.31 | 1.00 | 1.31 | 26.9% |
| 2 | FPOX-10 | 1 | 3.38 | 0.78 | 4.33 | 46.0% |
| 3 | FPOX-11 | 3 | 4.61 | 0.58 | 7.95 | 14.9% |
| 4 | FPOX-13 | 4 | 4.72 | 0.65 | 7.26 | 45.9% |
| 5 | FPOX-14 | 5 | 5.31 | 0.75 | 7.08 | 64.4% |
| 6 | FPOX-15 | 6 | 5.15 | 0.70 | 7.36 | 79.0% |

Table 1 above shows the substrate selectivity and heat resistance of various mutant fructosyl peptide oxidases. In Table 1 above, the α-FVH activity and ε-FK activity represent relative values when the ε-FK activity of FPOX-9 is taken as 1.00, and the number of additional mutations represents the number of substitutions made to FPOX-9.

Example 3

Obtaining Mutant Fructosyl Peptide Oxidases

The E. coli XL1-Blue strain carrying FPOX-9 obtained in Example 2 was inoculated into ten test tubes containing 10 mL of LB medium containing 50 mg/L of ampicillin, and they were shake-cultured at 30° C. for 24 hours. Each of the culture solutions was transferred into ten Erlenmeyer flasks containing 300 mL of LB medium containing 50 mg/L of ampicillin and 20 mg/L of IPTG, and shake-cultured at 30° C. for 24 hours.

Approximately 3,000 mL of the culture solution was collected, and the bacterial cells were collected by centrifugation at 10,000×g for 15 minutes. The bacterial cells were suspended in approximately 50 mL of 10 mmol/L phosphate buffer (pH 7.0), and the bacterial cells were disrupted for one minute while cooling on ice using an ultrasonic homogenizer. Disruption under the same conditions was further repeated nine times. This bacterial cell lysate was centrifuged at 10,000×g for 15 minutes, and the obtained supernatant was used as the crude enzyme extract.

To the crude enzyme extract, solid ammonium sulfate was added to obtain 60% saturation, and the mixture was kept stirring for two hours while cooling on ice to sufficiently precipitate the enzyme protein of interest. Subsequently, the precipitates were collected by centrifugation at 10,000×g for 15 minutes. The precipitates were dissolved in approximately 20 mL of 10 mmol/L phosphate buffer (pH 7.0), and this solution was dialyzed in a cold place overnight against 5,000 mL of the same buffer.

The dialyzed enzyme solution was loaded onto a 10×100 cm column packed with DEAE-Toyopearl (Toyobo Co.), which was equilibrated in advance using 10 mmol/L phosphate buffer (pH 7.0), and was washed further with the same buffer. The enzyme of interest passed through the column without being adsorbed. On the other hand, most of the contaminating proteins were adsorbed onto the column. As a result, as shown in Table 2, the enzyme of interest was purified approximately 50-fold with a yield of 31%. Similarly, the E. coli XL1-Blue strain carrying FPOX-15 obtained in Example 2 was subjected to a series of purification steps to obtain a solution of purified FPOX-15.

TABLE 2

| No. | STEP | AMOUNT OF TOTAL PROTEIN (mg) | TOTAL ACTIVITY (units) | SPECIFIC ACTIVITY (u/mg) | PERCENTAGE OF RECOVERED ACTIVITY (%) | PURIFICATION LEVEL (fold) |
|---|---|---|---|---|---|---|
| 1 | CELL EXTRACT | 3940.0 | 1196 | 0.3 | 100.0 | 1 |
| 2 | AMMONIUM SULFATE PRECIPITATION | 3065.0 | 933 | 0.3 | 78.0 | 1 |

TABLE 2-continued

| No. | STEP | AMOUNT OF TOTAL PROTEIN (mg) | TOTAL ACTIVITY (units) | SPECIFIC ACTIVITY (u/mg) | PERCENTAGE OF RECOVERED ACTIVITY (%) | PURIFICATION LEVEL (fold) |
|---|---|---|---|---|---|---|
| 3 | DEAE-FLOW THROUGH | 93.2 | 751 | 8.1 | 62.8 | 27 |
| 4 | AMMONIUM SULFATE CONCENTRATION | 24.9 | 374 | 15.0 | 31.3 | 50 |

Table 2 above shows the state of FPOX-9 in each of the steps of the purification of fructosyl peptide oxidase FPOX-9.

Example 4

Km Values of the Fructosyl Peptide Oxidase FPOX-9

Substrate specificity of the novel FPOX-9 obtained in Example 2 to glycated peptides and/or glycated amino acids were measured using the following Reagent 1 to Reagent 3.
Reagent 1

| Tris buffer (pH 7.5) | 100 mmol/L |
|---|---|

Reagent 2

| Tris buffer (pH 7.5) | 100 mmol/L |
|---|---|
| fructosyl peptide oxidase FPOX-9 | 2 μL |
| 4-aminoantipyrine | 0.5 mmol/L |
| TOOS | 0.2 mmol/L |
| peroxidase (horseradish-derived) | 10 U/mL |

Herein, the FPOX-9 solution used was the one prepared in Example 3.
Reagent 3

| Tris buffer (pH 7.5) | 100 mmol/L |
|---|---|
| α-FVH, α-FV or ε-FK | X mmol/L |

(When α-FVH or α-FV is used, X = 0, 0.05, 0.1, 0.5, 1, 2, 5, 10)
(When ε-FK is used, X = 0, 1, 2, 5, 10, 20, 40, 50, 80, 100)

As substrates, glycated peptide α-FVH as well as glycated amino acids ε-FK and α-FV were used.

α-FVH solutions and α-FV solutions were prepared using Tris buffer to obtain each of the following concentrations in Reagent 3: 0, 0.05, 0.1, 0.5, 1, 2, 5, and 10 mmol/L. ε-FK solutions were prepared using Tris buffer to obtain each of the following concentrations in Reagent 3: 0, 1, 2, 5, 10, 20, 40, 50, 80, and 100 mmol/L.

170 μL of Reagent 2 was added to 10 μL of Reagent 1, and after the reaction at 37° C. for five minutes, 20 μL of Reagent 3 was added, and the reaction was further continued at 37° C. for five minutes, a total of ten minutes. The absorbance at 546 nm (main wavelength)/800 nm (sub-wavelength) for 0 mmol/L at 5.4 minutes after starting the reaction was defined as $A_0'$ (Abs), and the absorbance at 546 nm (main wavelength)/800 nm (sub-wavelength) for each substrate concentration at 5.4 minutes after starting the reaction was defined as $A_0^x$ (Abs), and $\Delta A_0$ was calculated according to Equation (I).

(Mathematical Expression 1)

$$\Delta A_0 = A_0^x - A_0'(Abs) \quad (I)$$

The absorbance at 546 nm (main wavelength)/800 nm (sub-wavelength) for 0 mmol/L at 6.6 minutes after starting the reaction was defined as $A_s'$ (Abs), and the absorbance at 546 nm (main wavelength)/800 nm (sub-wavelength) for each substrate concentration at 6.6 minutes after starting the reaction was defined as $A_s^x$ (Abs), and $\Delta A_s$ was calculated according to Equation (II).

(Mathematical Expression 2)

$$\Delta A_s = A_s^x - A_s'(Abs) \quad (II)$$

The enzyme activity (U/mL) for each substrate concentration was calculated by substituting the obtained $\Delta A_0$ and $\Delta A_s$, total amount of reaction solution (0.2 mL), molar extinction coefficient of TOOS (39,200), reaction time (1.2 minutes), and the light path length of the reaction cuvette (0.5 cm) into Equation (III).

(Mathematical Expression 3)

$$\text{Enzyme activity(U/mL)} = \{(\Delta A_s - \Delta A_0) \times \text{total amount of reaction solution(mL)}\} / \{\text{molar extinction coefficient } \epsilon / 1000 \times \text{amount of enzyme solution(mL)} \times 0.5 \times \text{reaction time(min)} \times \text{light path length(cm)}\} \quad (III)$$

For each of the substrates α-FVH, ε-FK, and α-FV, a plot was produced with substrate concentration (mmol/L) on the horizontal axis and the corresponding enzyme activity (U/mL) on the vertical axis, and the substrate concentration corresponding to ½ of the maximum enzyme activity was calculated as the Km value (Michaelis constant). The results are shown in Table 3.

TABLE 3

| | SUBSTRATE | | |
|---|---|---|---|
| | α-FVH | α-FV | ε-FK |
| Km (mmol/L) | 0.5 | 0.6 | 4.0 |

Table 3 above shows the Km values of the fructosyl peptide oxidase FPOX-9 towards each type of substrate. Table 3 clearly indicates that the fructosyl peptide oxidase of the present invention is an enzyme that has high substrate specificity towards α-FVH and α-FV, and difficulty reacts with ε-FK.

Example 5

Mutations on the Fructosyl Peptide Oxidase FPOX-9 and Substrate Specificity of the Mutants Introduction of nucleotide substitutions and full-length amplification were carried out simultaneously by a PCR method that uses the "GeneMorph II Random Mutagenesis Kit" by using pTrcFPOX-9 as the template DNA and primers (SEQ ID NOs: 5 and 6) that correspond to the regions corresponding to the 5'-side upstream region and the 3'-side downstream region of the fructosyl peptide oxidase gene.

The PCR product was cleaved using NcoI and BamHI, then purified using a PureLink PCR Purification Kit (Invitrogen Corp.), ligated into the NcoI and BamHI sites of pTrc99A, and then this was used to transform the *E. coli* XL1-Blue strain.

Colonies (transformants) that grew when cultured overnight on a plate containing an LB medium containing 50 mg/L of ampicillin were picked. They were cultured at 30° C. for 18 hours using a 24-well culture plate (manufactured by Sumitomo Bakelite Co.) containing 2 mL of LB medium containing 50 mg/L of ampicillin BugBuster (manufactured by Novagen) was added to the medium, and after bacterial cell lysis and centrifugation, the enzyme activity towards two types of substrates (ε-FK and α-FVH) were measured using this supernatant solution as the enzyme source.

Meanwhile, plasmids were prepared from each transformant, and the nucleotide sequence of the fructosyl peptide oxidase gene portion was decoded using a DNA sequencer. Then the changes in substrate specificity were correlated with changes in the nucleotide sequences (amino acid sequences). The results are shown in Table 4.

TABLE 4

| No. | MUTATION | | | α-FVH ACTIVITY | ε-FK ACTIVITY | FVH/FK ACTIVITY RATIO | MUTANT |
|---|---|---|---|---|---|---|---|
| | AMINO ACID No. | BEFORE | AFTER | | | | |
| 1 | | | | 1.31 | 1.00 | 1.31 | FPOX-9 |
| 2 | 59 | Ser | Gly | 3.38 | 0.78 | 4.33 | FPOX-10 |
| 3 | 140 | Phe | Cys | 0.80 | 0.47 | 1.70 | |
| 4 | 328 | Ala | Val | 1.15 | 0.68 | 1.69 | |
| 5 | 358 | Leu | Met | 0.89 | 0.60 | 1.48 | |
| 6 | 366 | Lys | Agr | 1.16 | 1.22 | 0.95 | |
| 7 | 389 | Val | Leu | 0.85 | 0.87 | 0.97 | |

In the table shown above, α-FVH activity and ε-FK activity represent relative values when the ε-FK activity of FPOX-9 is taken to be 1.00. Table 4 shows that even when amino acid mutations are introduced into FPOX-9, the activity ratio of α-FVH activity to ε-FK activity (FVH/FK) of the mutants is not changed or increases as compared to that of FPOX-9.

Example 6

Km Values of the Fructosyl Peptide Oxidase FPOX-15

The substrate specificity of FPOX-15 obtained in Example 2 to glycated peptides and/or glycated amino acids was measured using the following Reagent 1 to Reagent 3.

Reagent 1

| | |
|---|---|
| sodium dihydrogen phosphate (pH 8.0) | 100 mmol/L |
| fructosyl peptide oxidase FPOX-15 | 2 μL |

Herein, for the FPOX-15 solution, a solution produced by four-fold dilution of the solution obtained in Example 3 was used.

Reagent 2

| | |
|---|---|
| sodium dihydrogen phosphate (pH 6.0, pH 7.0, or pH 8.0) | 100 mmol/L |
| peroxidase (horseradish-derived) | 3 U/mL |
| 4-aminoantipyrine | 0.5 mmol/L |
| EMSE | 0.4 mmol/L |

Reagent 3

| | |
|---|---|
| α-FVH, α-FV or ε-FK | X mmol/L |

(When α-FVH or α-FV is used, X = 0, 2, 2.5, 3, 3.66)
(When ε-FK is used, X = 0, 20, 30, 40, 50)

As substrates, glycated peptide α-FVH as well as glycated amino acids ε-FK and α-FV were used.

α-FVH solutions and α-FV solutions were prepared using distilled water to obtain the following concentrations in Reagent 3: 0, 2, 2.5, 3, and 3.66 mmol/L. ε-FK solution was prepared using distilled water to obtain the following concentrations in Reagent 3: 0, 20, 30, 40, and 50 mmol/L.

150 μL of Reagent 2 was added to 5 μL of Reagent 1, and after the reaction at 37° C. for five minutes, 20 μL of Reagent 3 was added, and the reaction was further continued at 37° C. for five minutes, a total of ten minutes. The absorbance at 546 nm (main wavelength)/700 nm (sub-wavelength) for 0 mmol/L at 5.4 minutes after starting the reaction was defined as $A_0'$ (Abs), and the absorbance at 546 nm (main wavelength)/700 nm (sub-wavelength) for each substrate concentration at 5.4 minutes after starting the reaction was defined as $A_0^x$ (Abs), and $\Delta A_0$ was calculated according to Equation (I).

(Mathematical Expression 1)

$$\Delta A_0 = A_0^x - A_0'(Abs) \quad \quad (I)$$

The absorbance at 546 nm (main wavelength)/700 nm (sub-wavelength) for 0 mmol/L at 6.6 minutes after starting the reaction was defined as $A_s'$ (Abs), and the absorbance at 546 nm (main wavelength)/700 nm (sub-wavelength) for each substrate concentration at 6.6 minutes after starting the reaction was defined as $A_s^x$ (Abs), and $\Delta A_s$ was calculated according to Equation (II).

(Mathematical Expression 2)

$$\Delta A_s = A_s^x - A_s'(Abs) \quad \quad (II)$$

The enzyme activity (U/mL) for each substrate concentration was calculated by substituting the obtained $\Delta A_0$ and $\Delta A_s$, total amount of reaction solution (0.2 mL), molar extinction coefficient of EMSE (33,800), reaction time (1.2 minutes), and the light path length of the reaction cuvette (0.5 cm) into Equation (III).

(Mathematical Expression 3)

Enzyme activity(U/mL)={($\Delta A_s - \Delta A_0$)×total amount of reaction solution(mL)}/{molar extinction coefficient ε/1000×amount of enzyme solution(mL)× 0.5×reaction time(min)×light path length(cm)}     (III)

For each of the substrates α-FVH, ε-FK, and α-FV, a plot was produced with substrate concentration (mmol/L) on the horizontal axis and the corresponding enzyme activity (U/mL) on the vertical axis, and the substrate concentration corresponding to ½ of the maximum enzyme activity was calculated as the Km value (Michaelis constant). The results are shown in Table 5.

TABLE 5

| | Km (mmol/L) | | |
|---|---|---|---|
| | SUBSTRATE | | |
| | α-FVH | α-FV | ε-FK |
| pH 6.0 | 0.4 | 0.2 | 23.2 |
| pH 7.0 | 0.5 | 0.3 | 19.2 |
| pH 8.0 | 0.8 | 0.3 | 9.6 |

Table 5 above shows the Km values of the fructosyl peptide oxidase FPOX-15 towards each type of substrate. Table 5 clearly indicates that the fructosyl peptide oxidase of the present invention is an enzyme that has high substrate specificity towards α-FVH and α-FV and low substrate specificity towards ε-FK.

Example 7

Isoelectric Point pI of Fructosyl Peptide Oxidases (FPOX-9 and FPOX-15)

Each of the 1 mg/mL phosphate buffer (pH7.0) solutions (3 μL) of FPOX-9 and FPOX-15 was applied to an isoelectric focusing gel of the Phast System (fully automatic electrophoresis system, GE Healthcare), and electrophoresis, staining, and destaining operations were carried out according to the operating procedure to determine the pI of each fructosyl peptide oxidase. The results are shown in Table 6.

TABLE 6

| | pI |
|---|---|
| FPOX-9 | 8.2 |
| FPOX-15 | 7.8 |

As shown in Table 6, the pI values of the fructosyl peptide oxidases FPOX-9 and FPOX-15 were found to be slightly on the alkaline side.

Example 8

Effect of the pH on the Stability of the Fructosyl Peptide Oxidases FPOX-9 and FPOX-15

The effects of the pH on the stability of the fructosyl peptide oxidases FPOX-9 and FPOX-15 were evaluated using the following Reagent 1 to Reagent 3. For the evaluation, each of a reagent immediately after preparation, a reagent stored for 24 hours (one day) at 30° C. after preparation, and a reagent stored for 5 days at 30° C. after preparation was used as Reagent 1.
Reagent 1

| Bis-Tris (pH 5.0, pH 6.0, pH 7.0, or pH 8.0) | 100 mmol/L |
| Fructosyl peptide oxidase FPOX-9 or FPOX-15 | 2 μL |

Herein, as the FPOX-9 solution, a solution produced by 20-fold dilution of the solution obtained in Example 3 was used, and as the FPOX-15 solution, a solution produced by 20-fold dilution of the solution obtained in Example 3 was used.

Reagent 2

| sodium dihydrogen phosphate (pH 6.0, pH 7.0, or pH 8.0) | 100 mmol/L |
| peroxidase (horseradish-derived) | 3 U/mL |
| 4-aminoantipyrine | 0.5 mmol/L |
| EMSE | 0.4 mmol/L |

Reagent 3

| α-FG (fructosyl glycine) | 0 or 15 mmol/L |

The glycated amino acid α-FG was used as the substrate.

150 μL of Reagent 2 was added to 5 μL of Reagent 1, and after the reaction at 37° C. for five minutes, 20 μL of Reagent 3 was added, and the reaction was further continued at 37° C. for five minutes, a total of ten minutes. The absorbance at 546 nm (main wavelength)/700 nm (sub-wavelength) for 0 mmol/L at 5.4 minutes after starting the reaction was defined as $A_0'$ (Abs), and the absorbance at 546 nm (main wavelength)/700 nm (sub-wavelength) for 15 mmol/L substrate at 5.4 minutes after starting the reaction was defined as $A_0^x$ (Abs), and $\Delta A_0$ was calculated according to Equation (I).

(Mathematical Expression 1)

$$\Delta A_0 = A_0^x - A_0'(Abs) \quad (I)$$

The absorbance at 546 nm (main wavelength)/700 nm (sub-wavelength) for 0 mmol/L at 6.6 minutes after starting the reaction was defined as $A_s'$ (Abs), and the absorbance at 546 nm (main wavelength)/700 nm (sub-wavelength) for 15 mmol/L at 6.6 minutes after starting the reaction was defined as $A_s^x$ (Abs), and $\Delta A_s$ was calculated according to Equation (II).

(Mathematical Expression 2)

$$\Delta A_s = A_s^x - A_s'(Abs) \quad (II)$$

The enzyme activity (U/mL) for 15 mmol/L substrate was calculated by substituting the obtained $\Delta A_0$ and $\Delta A_s$, total amount of reaction solution (0.2 mL), molar extinction coefficient of EMSE (33,800), reaction time (1.2 minutes), and the light path length of the reaction cuvette (0.5 cm) into Equation (III).

(Mathematical Expression 3)

Enzyme activity(U/mL)={($\Delta A_s - \Delta A_0$)×total amount of reaction solution(mL)}/{molar extinction coefficient ε/1000×amount of enzyme solution(mL)× 0.5×reaction time(min)×light path length(cm)} (III)

This series of operations were carried out for the reagent immediately after preparation, the reagent stored for 24 hours (one day) at 30° C., and the reagent stored for 5 days at 30° C., respectively, and based on the enzyme activity $E_{0\,day}$ in the reagent immediately after preparation, the enzyme activity $E_{1\,day}$ in the reagent stored for 24 hours at 30° C., and the enzyme activity $E_{5\,day}$ in the reagent stored for 5 days at 30° C., the percentage of the remaining enzyme activity (%) E' of the reagent stored for 24 hours (one day) at 30° C. and of the reagent stored for 5 days at 30° C. with respect to the reagent immediately after preparation was calculated according to Equation (IV). The results are shown in Table 7 and Table 8.

(Mathematical Expression 4)

Percentage of remaining enzyme activity
$$E'(\%) = (E_{1\,day} \text{ or } E_{5\,day})/E_{0\,day} \times 100 \quad (IV)$$

TABLE 7

PERCENTAGE OF REMAINING ENZYME ACTIVITY OF FPOX-9

| pH | 0 day (%) | 30° C., 1 day (%) | 30° C., 5 days (%) |
|---|---|---|---|
| pH 5.0 | 100 | 97 | 83 |
| pH 6.0 | 100 | 96 | 94 |
| pH 7.0 | 100 | 97 | 84 |
| pH 8.0 | 100 | 87 | 45 |

TABLE 8

PERCENTAGE OF REMAINING ENZYME ACTIVITY OF FPOX-15

| pH | 0 day (%) | 30° C., 1 day (%) | 30° C., 5 days (%) |
|---|---|---|---|
| pH 5.0 | 100 | 95 | 83 |
| pH 6.0 | 100 | 104 | 101 |
| pH 7.0 | 100 | 97 | 94 |
| pH 8.0 | 100 | 95 | 70 |

Table 7 shows the effect of the pH on the stability of the fructosyl peptide oxidase FPOX-9 and Table 8 shows the effect of the pH on the stability of the fructosyl peptide oxidase FPOX-15. As is clear from Tables 7 and 8, the fructosyl peptide oxidases FAOX-9 and FPOX-15 of the present invention were found to be stable under any of the following pHs: pH 5.0, pH 6.0, pH 7.0, and pH 8.0.

Example 9

Effects of Metals on the Stability of Fructosyl Peptide Oxidases FPOX-9 and FPOX-15

The effects of metals on the stability of the fructosyl peptide oxidases FPOX-9 and FPOX-15 were evaluated using the following Reagent 1 to Reagent 3. For the evaluation, each of a reagent immediately after preparation, a reagent stored for 24 hours (one day) at 5° C. after preparation, and a reagent stored for 24 hours (one day) at 30° C. after preparation was used as Reagent 1.

Reagent 1

| | |
|---|---|
| Bis-Tris (pH 7.0) | 100 mmol/L |
| Fructosyl peptide oxidase FPOX-9 or FPOX-15 | 2 µL |
| Metal ion | X mmol/L |

(When the metal ion is $Na^+$, $K^+$, or $Li^+$: X=100; when the metal ion is $Mg^{2+}$ or $Ca^{2+}$: X=10; and when the metal ion is $Cr^{3+}$, $Mn^{2+}$, $Fe^{3+}$, $Co^{2+}$, $Ni^{2+}$, $Cu^{2+}$, $Zn^{2+}$, $Ag^+$, $Cd^{2+}$, $Pb^{2+}$, $Ba^{2+}$, $Al^+$, or $Sr^{2+}$: X=0.1)

Herein, as the FPOX-9 solution, a solution produced by 20-fold dilution of the solution obtained in Example 3 was used, and as the FPOX-15 solution, a solution produced by 100-fold dilution of the solution obtained in Example 3 was used.

Reagent 2

| | |
|---|---|
| sodium dihydrogen phosphate (pH 8.0) | 100 mmol/L |
| peroxidase (horseradish-derived) | 3 U/mL |
| 4-aminoantipyrine | 0.5 mmol/L |
| EMSE | 0.4 mmol/L |

Reagent 3

| | |
|---|---|
| α-FG (fructosyl glycine) | 0 or 15 mmol/L |

The glycated amino acid α-FG was used as the substrate.

150 µL of Reagent 2 was added to 5 µL of Reagent 1, and after the reaction at 37° C. for five minutes, 20 µL of Reagent 3 was added, and the reaction was further continued at 37° C. for five minutes, a total of ten minutes. The absorbance at 546 nm (main wavelength)/700 nm (sub-wavelength) for 0 mmol/L at 5.4 minutes after starting the reaction was defined as $A_0'$ (Abs), and the absorbance at 546 nm (main wavelength)/700 nm (sub-wavelength) for 15 mmol/L substrate at 5.4 minutes after starting the reaction was defined as $A_0^x$ (Abs), and $\Delta A_0$ was calculated according to Equation (I).

(Mathematical Expression 1)

$$\Delta A_0 = A_0^x - A_0'(Abs) \tag{I}$$

The absorbance at 546 nm (main wavelength)/700 nm (sub-wavelength) for 0 mmol/L at 6.6 minutes after starting the reaction was defined as $A_s'$ (Abs), and the absorbance at 546 nm (main wavelength)/700 nm (sub-wavelength) for 15 mmol/L at 6.6 minutes after starting the reaction was defined as $A_s^x$ (Abs), and $\Delta A_s$ was calculated according to Equation (II).

(Mathematical Expression 2)

$$\Delta A_s = A_s^x - A_s'(Abs) \tag{II}$$

The enzyme activity (U/mL) for 15 mmol/L substrate was calculated by substituting the obtained $\Delta A_0$ and $\Delta A_s$, total amount of reaction solution (0.2 mL), molar extinction coefficient of EMSE (33,800), reaction time (1.2 minutes), and the light path length of the reaction cuvette (0.5 cm) into Equation (III).

(Mathematical Expression 3)

$$\text{Enzyme activity(U/mL)} = \{(\Delta A_s - \Delta A_0) \times \text{total amount of reaction solution(mL)}\} / \{\text{molar extinction coefficient e/1000} \times \text{amount of enzyme solution(mL)} \times 0.5 \times \text{reaction time(min)} \times \text{light path length(cm)}\} \tag{III}$$

This series of operations were carried out for the reagent immediately after preparation, the reagent stored for 24 hours (one day) at 5° C., and the reagent stored for 24 hours (one day) at 30° C., respectively, and based on the enzyme activity $E'_{0\,day}$ in the reagent immediately after preparation and the enzyme activity $E'_{1\,day}$ in the reagent stored for 24 hours (one day) at 5° C. or 30° C., the percentage of the remaining enzyme activity (%) E" of the reagent stored for 24 hours (one day) at 5° C. or 30° C. to the reagent immediately after preparation was calculated according to Equation (V). The results are shown in Table 9 and Table 10.

(Mathematical Expression 5)

Percentage of remaining enzyme activity
$$E''(\%) = (E'_{1\,day} / E'_{0\,day}) \times 100 \tag{V}$$

TABLE 9

PERCENTAGE OF REMAINING ENZYME ACTIVITY OF FPOX-9

| | IMMEDIATELY AFTER PREPARATION | 5° C., 1 DAY | 30° C., 1 DAY |
|---|---|---|---|
| NO ADDITION | 100 | 101 | 97 |
| 100 mmol/L $Na^+$ | 100 | 103 | 94 |
| $K^+$ | 100 | 102 | 99 |

TABLE 9-continued

PERCENTAGE OF REMAINING ENZYME ACTIVITY OF FPOX-9

|  |  | IMMEDIATELY AFTER PREPARATION | 5° C., 1 DAY | 30° C., 1 DAY |
|---|---|---|---|---|
|  | Li$^+$ | 100 | 94 | 96 |
| 10 mmol/L | Mg$^{2+}$ | 100 | 107 | 97 |
|  | Ca$^{2+}$ | 100 | 99 | 97 |
| 0.1 mmol/L | Cr$^{3+}$ | 100 | 93 | 93 |
|  | Mn$^{2+}$ | 100 | 102 | 98 |
|  | Fe$^{3+}$ | 100 | 103 | 97 |
|  | Co$^{2+}$ | 100 | 93 | 93 |
|  | Ni$^{2+}$ | 100 | 109 | 100 |
|  | Cu$^{2+}$ | 100 | 98 | 91 |
|  | Zn$^{2+}$ | 100 | 101 | 99 |
|  | Ag$^+$ | 100 | 101 | 96 |
|  | Cd$^{2+}$ | 100 | 101 | 98 |
|  | Pb$^{2+}$ | 100 | 94 | 99 |
|  | Ba$^{2+}$ | 100 | 103 | 98 |
|  | Al$^{3+}$ | 100 | 92 | 94 |
|  | Sr$^{2+}$ | 100 | 96 | 97 |

TABLE 10

PERCENTAGE OF REMAINING ENZYME ACTIVITY OF FPOX-15

|  |  | IMMEDIATELY AFTER PREPARATION | 5° C., 1 DAY | 30° C., 1 DAY |
|---|---|---|---|---|
| NO ADDITION |  | 100 | 94 | 97 |
| 100 mmol/L | Na$^+$ | 100 | 99 | 102 |
|  | K$^+$ | 100 | 106 | 104 |
|  | Li$^+$ | 100 | 104 | 104 |
| 10 mmol/L | Mg$^{2+}$ | 100 | 108 | 104 |
|  | Ca$^{2+}$ | 100 | 105 | 104 |
| 0.1 mmol/L | Cr$^{3+}$ | 100 | 102 | 101 |
|  | Mn$^{2+}$ | 100 | 99 | 100 |
|  | Fe$^{3+}$ | 100 | 102 | 102 |
|  | Co$^{2+}$ | 100 | 95 | 107 |
|  | Ni$^{2+}$ | 100 | 101 | 101 |
|  | Cu$^{2+}$ | 100 | 100 | 79 |
|  | Zn$^{2+}$ | 100 | 102 | 100 |
|  | Ag$^+$ | 100 | 99 | 102 |
|  | Cd$^{2+}$ | 100 | 101 | 96 |
|  | Pb$^{2+}$ | 100 | 100 | 101 |
|  | Ba$^{2+}$ | 100 | 100 | 100 |
|  | Al$^{3+}$ | 100 | 91 | 91 |
|  | Sr$^{2+}$ | 100 | 102 | 103 |

Table 9 shows the effects of metals on the stability of the fructosyl peptide oxidase FPOX-9 and Table 10 shows the effects of metals on the stability of the fructosyl peptide oxidase FPOX-15. As is clear from Tables 9 and 10, the fructosyl peptide oxidases FAOX-9 and FPOX-15 of the present invention were found to be stable in the co-presence of each of the metal species.

INDUSTRIAL APPLICABILITY

The present invention provides novel proteins useful for diagnosing lifestyle diseases such as diabetes, DNAs encoding the proteins, methods for producing the proteins, as well as methods for measuring glycated proteins using the proteins, and reagents for measuring glycated proteins comprising the proteins.

SEQUENCE LISTING FREE TEXT

SEQ ID NO: 5—Description of Artificial Sequence: Synthetic DNA

SEQ ID NO: 6—Description of Artificial Sequence: Synthetic DNA

The invention claimed is:

1. A DNA of any one of [1] or [2] below:
   [1] a DNA encoding the protein of any one of (i) to (iv) below;
      (i) a protein comprising the amino acid sequence represented by SEQ ID NO:1;
      (ii) a protein comprising an amino acid sequence with one to ten amino acid deletions, substitutions, or additions in the amino acid sequence represented by SEQ ID NO:1, and having fructosyl peptide oxidase activity;
      (iii) a protein comprising an amino acid sequence having 99% or higher homology to the amino acid sequence represented by SEQ ID NO:1, and having fructosyl peptide oxidase activity; and
      (iv) a protein having fructosyl peptide oxidase activity, which is encoded by an expression plasmid harbored by the *Escherichia coli* XL1-Blue MRF' strain deposited under Accession No. FERM BP-11026;
   [2] a DNA comprising the nucleotide sequence represented by SEQ ID NO: 2.

2. The DNA of claim 1, encoding a protein comprising the amino acid sequence represented by SEQ ID NO: 3.

3. The DNA of claim 1, comprising the nucleotide sequence represented by SEQ ID NO: 4.

4. A recombinant DNA comprising the DNA of claim 1.

5. A recombinant DNA comprising the DNA of claim 2.

6. A recombinant DNA comprising the DNA of claim 3.

7. A transformant comprising the recombinant DNA of claim 4.

8. A transformant comprising the recombinant DNA of claim 5.

9. A transformant comprising the recombinant DNA of claim 6.

10. A method for producing a protein of any one of [1] to [4] below:
   [1] a protein comprising the amino acid sequence represented by SEQ ID NO: 1;
   [2] a protein comprising an amino acid sequence with one to ten amino acid deletions, substitutions, or additions in the amino acid sequence represented by SEQ ID NO: 1, and having fructosyl peptide oxidase activity;

[3] a protein comprising an amino acid sequence having 99% or higher homology to the amino acid sequence represented by SEQ ID NO: 1, and having fructosyl peptide oxidase activity; and

[4] a protein having fructosyl peptide oxidase activity, which is encoded by an expression plasmid harbored by the *Escherichia coli* XL1-Blue MRF' strain deposited under Accession No. FERM BP-11026, wherein the transformant of claim 7 is cultured in a medium, the protein is produced and accumulated in the culture, and the protein is collected from the culture.

11. A method for producing a protein of any one of [1] to [4] below:

[1] a protein comprising the amino acid sequence represented by SEQ ID NO: 1;

[2] a protein comprising an amino acid sequence with one to ten amino acid deletions, substitutions, or additions in the amino acid sequence represented by SEQ ID NO: 1, and having fructosyl peptide oxidase activity;

[3] a protein comprising an amino acid sequence having 99% or higher homology to the amino acid sequence represented by SEQ ID NO: 1, and having fructosyl peptide oxidase activity; and

[4] a protein having fructosyl peptide oxidase activity, which is encoded by an expression plasmid harbored by the *Escherichia coli* XL1-Blue MRF' strain deposited under Accession No. FERM BP-11026, wherein the transformant of claim 8 is cultured in a medium, the protein is produced and accumulated in the culture, and the protein is collected from the culture.

12. A method for producing a protein of any one of [1] to [4] below:

[1] a protein comprising the amino acid sequence represented by SEQ ID NO: 1;

[2] a protein comprising an amino acid sequence with one to ten amino acid deletions, substitutions, or additions in the amino acid sequence represented by SEQ ID NO: 1, and having fructosyl peptide oxidase activity;

[3] a protein comprising an amino acid sequence having 99% or higher homology to the amino acid sequence represented by SEQ ID NO: 1, and having fructosyl peptide oxidase activity; and

[4] a protein having fructosyl peptide oxidase activity, which is encoded by an expression plasmid harbored by the *Escherichia coli* XL1-Blue MRF' strain deposited under Accession No. FERM BP-11026, wherein the transformant of claim 9 is cultured in a medium, the protein is produced and accumulated in the culture, and the protein is collected from the culture.

13. The method of claim 10, wherein the protein comprises the amino acid sequence represented by SEQ ID NO: 3.

14. The method of claim 11, wherein the protein comprises the amino acid sequence represented by SEQ ID NO: 3.

15. The method of claim 12, wherein the protein comprises the amino acid sequence represented by SEQ ID NO: 3.

16. *Escherichia coli* XL1-Blue MRF' strain deposited under Accession No. FERM BP-11026.

* * * * *

UNITED STATES PATENT AND TRADEMARK OFFICE
CERTIFICATE OF CORRECTION

PATENT NO. : 8,790,905 B2  Page 1 of 1
APPLICATION NO. : 13/633410
DATED : July 29, 2014
INVENTOR(S) : Kazuo Aisaka et al.

It is certified that error appears in the above-identified patent and that said Letters Patent is hereby corrected as shown below:

Title Page

Applicants, item 71, remove "Toshiko Aisaka, Machida (JP)".

Inventors, item 72, add "Toshiko Aisaka, Machida (JP) Legal Representative".

Abstract, item 57, Part 2, replace "comprising the of" with --comprising the sequence of--.

In the Specification

Column 6, Line 31, replace "1 mmol" with --1 µmol--.

Column 11, Line 53, replace "PHOS" with --PHO5--.

Column 27, Line 2, replace "ampicillin BugBuster" with --ampicillin. BugBuster--.

Column 31, Line 9, replace "ampicillin BugBuster" with --ampicillin. BugBuster--.

Column 35, Line 27, replace "FAOX-9" with --FPOX-9--.

Column 35, Line 54, replace "$Al^+$" with --$Al^{3+}$--.

Column 38, Line 21, replace "FAOX-9" with --FPOX-9--.

Signed and Sealed this
Sixteenth Day of December, 2014

Michelle K. Lee
*Deputy Director of the United States Patent and Trademark Office*

```
SEQUENCE LISTING

<160> NUMBER OF SEQ ID NOS: 6

<210> SEQ ID NO 1
<211> LENGTH: 438
<212> TYPE: PRT
<213> ORGANISM: Artificial
<220> FEATURE:
<223> OTHER INFORMATION: an artificially synthesized sequence

<400> SEQUENCE: 1

Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
            20                  25                  30

Pro Ser Asn Ile Thr Val Leu Asp Thr Tyr Pro Ile Pro Ser Ala Gln
        35                  40                  45

Ser Ala Gly Tyr Asp Leu Asn Lys Ile Met Ser Ile Arg Leu Arg Asn
    50                  55                  60

Lys Pro Asp Leu Gln Leu Tyr Leu Glu Ala Leu Asp Met Trp Lys Asn
65                  70                  75                  80

Asp Pro Leu Phe Lys Pro Phe Phe His Asn Val Gly Gln Met Asp Val
                85                  90                  95

Ser Ser Thr Glu Glu Gly Ile Lys Gly Leu Arg Met Arg Tyr Gln Ser
            100                 105                 110
```

Leu Leu Asp Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145                 150                 155                 160

Ala Ala Lys Ala Ile Asn Ala Ile Gly Gln Phe Leu Lys Glu Gln Gly
                165                 170                 175

Val Lys Phe Gly Phe Gly Gly Ala Gly Thr Phe Lys Lys Pro Leu Phe
            180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
                245                 250                 255

Thr Pro Val Ile Tyr Asp Gly Asp Tyr Gly Phe Phe Ile Glu Pro Asn
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Pro Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 2
<211> LENGTH: 1317
<212> TYPE: DNA
<213> ORGANISM: Artificial
<220> FEATURE:
<223> OTHER INFORMATION: an artificially synthesized sequence

<400> SEQUENCE: 2
atggcgcccc gagccaacac caaaatcatc gtcgtcggcg gcggcggcac aatgggctcg      60
tcgacagccc tacacctcct gcgcgccggc tacacgccgt ccaacatcac agtgctcgac     120
acgtacccta tcccttccgc acagtctgca ggctacgacc tgaacaaaat catgagcatc     180

```
aggctgcgca acaagcctga cttacaactc tatcttgagg cgctggacat gtggaaaaat      240
gatcctctat tcaagccgtt tttccacaat gttggacaga tggacgtctc ttcaacagaa      300
gaaggcatca aggtcttcg catgagatac cagtctcttc tcgacgcagg cattgggctc       360
gagaagacga atttcctgct ggaaagtgaa gacgagatcc tggctaaagc gccgcatttc      420
acgcgggagc agattaaagg ctggaaaggg ctgttctgtg gcgacggcgg ttggctcgct      480
gcagccaaag ccatcaatgc catcgggcag ttcctcaagg aacagggcgt caagtttgga      540
tttggcgggg ccggcacgtt caaaaagcca ctcttcgccg atgccgacga agacgtgc        600 atcggcgtcg aaactgtaga cggcacaaaa tactacgccg acaaggtcgt tctagcagct      660
ggtgcctgga gttcgacgtt ggtcgatctg gaggagcagt gcgtttcaaa ggcctgggtc      720
tttgcccaca tccaactgac gcccgctgaa gcagccgcgt acaagaacac tcctgttata      780
tacgacggtg actatgggtt tttcattgag ccgaatgaga acggcatcat aaaagtctgc      840
gacgaattcc ctggcttcac gcacttcaag atgcaccagc cgtacggctc accggtgccc      900
aaacccatct ctgtgcctcg ctcccatgcg aagcacccca cagatacata cccgcacgcg      960
tcggaggtca ccatcaaaaa ggctatcaac cggttcctgc cgaggttcaa tgacaaggaa     1020
ctgtttaaca gggccatgtg ctggtgcacc gataccgcgg atgcaaatct gcttgtttgt     1080
gagcatccac gctggaaggg gttttatctt gcaacagggg acagcgggca ttcgttcaag     1140
ttgctgccga atattggaaa gcacgttgtc gagttattgg aggggaggct ggaaagtgtg     1200
tttaaggatg cttggaggtg gaggcctggc agtggggatg cattaaagag tagacgggct     1260
gcgcctgcga aggacctggc ggatatgccg gggtggagga atgaggcaaa gatgtag        1317
```

<210> SEQ ID NO 3
<211> LENGTH: 438
<212> TYPE: PRT
<213> ORGANISM: Artificial
<220> FEATURE:
<223> OTHER INFORMATION: an artificially synthesized sequence

<400> SEQUENCE: 3

```
Met Ala Pro Arg Ala Asn Thr Lys Ile Ile Val Val Gly Gly Gly Gly
1               5                   10                  15

Thr Met Gly Ser Ser Thr Ala Leu His Leu Leu Arg Ala Gly Tyr Thr
                20                  25                  30

Pro Ser Asn Ile Thr Val Leu Asp Thr Tyr Pro Ile Pro Ser Ala Gln
            35                  40                  45

Ser Ala Gly Tyr Asp Leu Asn Lys Ile Phe Gly Ile Arg Leu Arg Asn
        50                  55                  60

Lys Pro Asp Leu Gln Leu Tyr Leu Glu Ala Leu Asp Met Trp Lys Asn
65                  70                  75                  80

Asp Pro Leu Phe Lys Pro Phe His Asn Val Gly Gln Met Asp Val
                85                  90                  95

Ser Ser Thr Glu Glu Gly Ile Lys Lys Leu Arg Met Arg Tyr Gln Ser
                100                 105                 110

Leu Leu Asp Ala Gly Ile Gly Leu Glu Lys Thr Asn Phe Leu Leu Glu
            115                 120                 125

Ser Glu Asp Glu Ile Leu Ala Lys Ala Pro His Phe Thr Arg Glu Gln
        130                 135                 140

Ile Lys Gly Trp Lys Gly Leu Phe Cys Gly Asp Gly Gly Trp Leu Ala
145                 150                 155                 160
```

Ala Ala Lys Ala Ile Asn Ala Ile Gly Gln Phe Leu Lys Glu Gln Gly
            165                 170                 175

Val Lys Phe Gly Phe Gly Glu Ala Gly Thr Phe Lys Lys Pro Leu Phe
        180                 185                 190

Ala Asp Ala Asp Glu Lys Thr Cys Ile Gly Val Glu Thr Val Asp Gly
        195                 200                 205

Thr Lys Tyr Tyr Ala Asp Lys Val Val Leu Ala Ala Gly Ala Trp Ser
    210                 215                 220

Ser Thr Leu Val Asp Leu Glu Glu Gln Cys Val Ser Lys Ala Trp Val
225                 230                 235                 240

Phe Ala His Ile Gln Leu Thr Pro Ala Glu Ala Ala Tyr Lys Asn
            245                 250                 255

Thr Pro Val Ile Tyr Asp Gly Asp Tyr Gly Phe Phe Ile Glu Pro Asp
            260                 265                 270

Glu Asn Gly Ile Ile Lys Val Cys Asp Glu Phe Pro Gly Phe Thr His
        275                 280                 285

Phe Lys Met His Gln Pro Tyr Gly Ser Pro Val Pro Lys Leu Ile Ser
290                 295                 300

Val Pro Arg Ser His Ala Lys His Pro Thr Asp Thr Tyr Pro His Ala
305                 310                 315                 320

Ser Glu Val Thr Ile Lys Lys Ala Ile Asn Arg Phe Leu Pro Arg Phe
                325                 330                 335

Asn Asp Lys Glu Leu Phe Asn Arg Ala Met Cys Trp Cys Thr Asp Thr
            340                 345                 350

Ala Asp Ala Asn Leu Leu Val Cys Glu His Pro Arg Trp Lys Gly Phe
        355                 360                 365

Tyr Leu Ala Thr Gly Asp Ser Gly His Ser Phe Lys Leu Leu Pro Asn
    370                 375                 380

Ile Gly Lys His Val Val Glu Leu Leu Glu Gly Arg Leu Glu Ser Val
385                 390                 395                 400

Phe Lys Asp Ala Trp Arg Trp Arg Pro Gly Ser Gly Asp Ala Leu Lys
                405                 410                 415

Ser Arg Arg Ala Ala Pro Ala Lys Asp Leu Ala Asp Met Pro Gly Trp
            420                 425                 430

Arg Asn Glu Ala Lys Met
        435

<210> SEQ ID NO 4
<211> LENGTH: 1317
<212> TYPE: DNA
<213> ORGANISM: Artificial
<220> FEATURE:
<223> OTHER INFORMATION: an artificially synthesized sequence

<400> SEQUENCE: 4
atggcgcccc gagccaacac caaaatcatc gtcgtcggcg gcggcggcac aatgggctcg    60
tcgacagccc tacacctcct gcgcgccggc tacacgccgt ccaacatcac agtgctcgac   120
acgtacccta tcccttccgc acagtctgca ggctacgacc tgaacaaaat cttcggcatc   180
aggctgcgca caagcctga cttacaactc tatcttgagg cgctggacat gtggaaaaat   240
gatcctctat tcaagccgtt tttccacaat gttggacaga tggacgtctc ttcaacagaa   300
gaaggcatca aaaagcttcg catgagatac cagtctcttc tcgacgcagg cattgggctc   360
gagaagacga atttcctgct ggaaagtgaa gacgagatcc tggctaaagc gccgcatttc   420
acgcgggagc agattaaagg ctggaaaggg ctgttctgtg gcgacggcgg ttggctcgct   480

```
gcagccaaag ccatcaatgc catcgggcag ttcctcaagg aacagggcgt caagtttgga    540
tttggcgagg ccggcacgtt caaaaagcca ctcttcgccg atgccgacga aagacgtgc    600 atcggcgtcg aaactgtaga cggcacaaaa tactacgccg acaaggtcgt tctagcagct    660
ggtgcctgga gttcgacgtt ggtcgatctg gaggagcagt gcgtttcaaa ggcctgggtc    720
tttgcccaca tccaactgac gcccgctgaa gcagccgcgt acaagaacac tcctgttata    780
tacgacggtg actatgggtt tttcattgag ccggacgaga acggcatcat aaaagtctgc    840
gacgaattcc ctggcttcac gcacttcaag atgcaccagc cgtacggctc accggtgccc    900
aaattgatct ctgtgcctcg ctcccatgcg aagcacccca cagatacata cccgcacgcg    960
tcggaggtca ccatcaaaaa ggctatcaac cggttcctgc cgaggttcaa tgacaaggaa   1020
ctgtttaaca gggccatgtg ctggtgcacc gataccgcgg atgcaaatct gcttgtttgt   1080
gagcatccac gctggaaggg gttttatctt gcaacagggg acagcgggca ttcgttcaag   1140
ttgctgccga atattggaaa gcacgttgtc gagttattgg aggggaggct ggaaagtgtg   1200
tttaaggatg cttggaggtg gaggcctggc agtggggatg cattaaagag tagacgggct   1260
gcgcctgcga aggacctggc ggatatgccg gggtggagga atgaggcaaa gatgtag      1317

<210> SEQ ID NO 5
<211> LENGTH: 27
<212> TYPE: DNA
<213> ORGANISM: Artificial
<220> FEATURE:
<223> OTHER INFORMATION: an artificially synthesized primer sequence

<400> SEQUENCE: 5
catgccatgg cgccccgagc caacacc                                         27

<210> SEQ ID NO 6
<211> LENGTH: 29
<212> TYPE: DNA
<213> ORGANISM: Artificial
<220> FEATURE:
<223> OTHER INFORMATION: an artificially synthesized primer sequence

<400> SEQUENCE: 6
cgcggatccc tacatctttg cctcattcc                                       29
```